United States Patent
Wan et al.

(10) Patent No.: US 11,710,139 B1
(45) Date of Patent: Jul. 25, 2023

(54) INDIVIDUAL TREATMENT EFFECT ESTIMATION UNDER HIGH-ORDER INTERFERENCE IN HYPERGRAPHS

(71) Applicant: Microsoft Technology Licensing, LLC, Redmond, WA (US)

(72) Inventors: Mengting Wan, Bellevue, WA (US); Jing Ma, Charlottesville, VA (US); Longqi Yang, Issaquah, WA (US); Brent Jaron Hecht, Redmond, WA (US); Jaime Teevan, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 17/682,200

(22) Filed: Feb. 28, 2022

(51) Int. Cl.
*G06N 3/04* (2023.01)
*G06Q 30/0201* (2023.01)
(Continued)

(52) U.S. Cl.
CPC ....... *G06Q 30/0201* (2013.01); *G06N 3/0464* (2023.01); *G06N 5/04* (2013.01); *G06Q 30/0631* (2013.01)

(58) Field of Classification Search
CPC .......... G06N 5/04; G06N 3/02; G06N 3/0464; G06Q 30/0201; G06Q 30/0256; G06Q 30/0631
See application file for complete search history.

(56) References Cited

U.S. PATENT DOCUMENTS 11,126,679 B2   9/2021  Shaabani et al.
2015/0347480 A1  12/2015  Smart
(Continued)

OTHER PUBLICATIONS

Ma, "Causal Inference under Networked Interference and Intervention Policy Enhancement", Proceedings of the 24th International Conference on Artificial Intelligence and Statistics (AISTATS) 2021, San Diego, California, USA. (Year: 2021).*
(Continued)

*Primary Examiner* — Dave Misir
(74) *Attorney, Agent, or Firm* — International IP Law Group, PLLC

(57) ABSTRACT

A computing system, computer-readable storage medium, and method for individual treatment effect (ITE) estimation under high-order interference in hypergraphs are described herein. The method includes accessing, via a processor, a hypergraph dataset including multi-way interactions among nodes within each hyperedge of a corresponding hypergraph, where the hypergraph dataset corresponds to a treatment assignment for each node. The method includes performing representation learning on the hypergraph dataset to control for confounders corresponding to features of each node and to learn a confounder representation for each node. The method also includes modeling a high-order interference representation for each node by propagating the learned confounder representation and the treatment assignment for each node through a hypergraph neural network. The method further includes estimating the ITE for each node under the treatment assignment based on the learned confounder representation and the modeled high-order interference representation for each node.

12 Claims, 8 Drawing Sheets

(51) Int. Cl.
    *G06N 5/04*        (2023.01)
    *G06Q 30/0601*     (2023.01)
    *G06N 3/0464*      (2023.01)

(56) References Cited

U.S. PATENT DOCUMENTS

2022/0286474 A1*  9/2022  Kuppa ................... G06N 20/20
2023/0037388 A1*  2/2023  Sakhinana ............. G16C 20/70

OTHER PUBLICATIONS

Yao, et al., "Representation Learning for Treatment Effect Estimation from Observational Data", In Proceedings of 32nd Conference on Neural Information Processing Systems, vol. 31, Dec. 3, 2018, 11 Pages.

Yilmaz, et al., "Geographic and Network Neighbors: Spillover Effects of Telecommunications Infrastructure", In Journal of Regional Science, vol. 42, Issue 2, Dec. 17, 2002, pp. 339-360.

Yoon, et al., "How Much and When do we Need Higher-Order Information in Hypergraphs? A Case Study on Hyperedge Prediction", In Proceedings of International World Wide Web Conference, Apr. 20, 2020, pp. 2627-2633.

Yuan, et al., "Causal Network Motifs: Identifying Heterogeneous Spillover Effects in A/B Tests", In Proceedings of International World Wide Web Conference, Apr. 19, 2021, pp. 3359-3370.

Zecevic, et al., "Relating Graph Neural Networks to Structural Causal Models", In Repository of arXiv:2109.04173v3, Oct. 22, 2021, 29 Pages.

Zhang, et al., "Beyond Link Prediction: Predicting Hyperlinks in Adjacency Space", In Proceedings of Thirty-Second AAAI Conference on Artificial Intelligence, vol. 32, Issue 1, Apr. 29, 2018, 8 Pages.

Zhang, et al., "Hyper-Sagnn: A Self-Attention Based Graph Neural Network for Hypergraphs", In Repository of https://arxiv.org/pdf/1911.02613.pdf, Nov. 11, 2019, 16 Pages.

Zheng, et al., "Exploration on the Spatial Spillover Effect of Infrastructure Network on Urbanization: A Case Study in Wuhan Urban Agglomeration", In Journal of Sustainable Cities and Society, vol. 47, May 1, 2019, 22 Pages.

Benson, et al., "Sequences of Sets", In Proceedings of the 24th ACM SIG KDD International Conference on Knowledge Discovery & Data Mining, Aug. 19-23, 2018, pp. 1148-1157.

Goodreads: Book Reviews, Recommendations, and Discussion, Retrieved From: https://web.archive.org/web/20220101231756/https://www.goodreads.com/, Jan. 1, 2022, 3 Pages.

Microsoft Teams, Retrieved from: https://web.archive.org/web/20210131004032/https:/www.microsoft.com/en-us/microsoft-teams/group-chat-software, Jan. 31, 2020, 6 Pages.

Ahluwalia, et al., "The Moderating Role of Commitment on the Spillover Effect of Marketing Communications", In Journal of Marketing research, vol. 38, Issue 4, Nov. 1, 2001, pp. 458-470.

Arbour, et al., "Inferring Network Effects from Observational Data", In Proceedings of the 22nd ACM SIGKDD International Conference on Knowledge Discovery and Data Mining, Aug. 13, 2016, pp. 715-724.

Aronow, et al., "Estimating Average Causal Effects Under General Interference, with Application to a Social Network Experiment", In Journal of the Annals of Applied Statistics, vol. 11, Issue 4, Dec. 2017, pp. 1912-1947.

Arya, et al., "Exploiting Relational Information in Social Networks Using Geometric Deep Learning on Hypergraphs", In Proceedings of the ACM on International Conference on Multimedia Retrieval, Jun. 11, 2018, pp. 117-125.

Awan, et al., "Almost-Matching-Exactly for Treatment Effect Estimation under Network Interference", Retrieved From: https://arxiv.org/pdf/2003.00964v1.pdf, Mar. 2, 2020, 37 Pages.

Bai, et al., "Hypergraph Convolution and Hypergraph Attention", In Journal of Pattern Recognition, vol. 110, Feb. 2021, 8 Pages.

Basse, et al., "Analyzing Two-Stage Experiments in the Presence of Interference", In Journal of the American Statistical Association, vol. 113, Issue 521, May 16, 2018, 33 Pages.

Benson, et al., "Simplicial Closure and Higher-Order Link Prediction", In Proceedings of the National Academy of Sciences, vol. 115, Issue 48, Nov. 9, 2018, pp. 11221-11230.

Bhattacharya, et al.,"Causal Inference Under Interference and Network Uncertainty", In Proceedings of the 35th Uncertainty in Artificial Intelligence Conference, Aug. 6, 2020, 11 Pages.

Brandes, et al., "Social Networks", In the Publication of Handbook of graph drawing visualization by CRC Press, 2013, pp. 805-839.

Ding, et al., "Be More with Less: Hypergraph Attention Networks for Inductive Text Classification", In Repository of arXiv:2011.00387v1, Nov. 1, 2020, 10 Pages.

Fatemi, et al., "Minimizing Interference and Selection Bias in Network Experiment Design", In Proceedings of the International AAAI Conference on Web and Social Media, vol. 14, May 26, 2020, pp. 176-186.

Feng, et al., "Hypergraph Neural Networks", In Proceedings of the AAAI Conference on Artificial Intelligence, vol. 33, Issue 01, Jul. 17, 2019, pp. 3558-3565.

Fisher, Ronald Aylmer, "Design of Experiments", In Journal of Br Med Journal, vol. 1, No. 3923, Mar. 14, 1936, p. 554.

Goldstein, et al., "Ethical Issues in Pragmatic Randomized Controlled Trials: A Review of The Recent Literature Identifies Gaps in Ethical Argumentation", In Publication of BMC Medical Ethics, vol. 19, Issue 1, Feb. 27, 2018, 10 Pages.

Gretton, et al., "Measuring Statistical Dependence with Hilbert-Schmidt Norms", In Proceedings of International Conference on Algorithmic Learning Theory, Jun. 2005, 16 Pages.

Guo, et al., "Learning Individual Causal Effects from Networked Observational Data", In Proceedings of the 13th International Conference on Web Search and Data Mining, Feb. 3, 2020, pp. 232-240.

Harada, et al., "Counterfactual Propagation for Semi-Supervised Individual Treatment Effect Estimation", Retrieved From: https://arxiv.org/pdf/2005.05099v1.pdf, May 11, 2020, 18 Pages.

Hill, Jennifer Lynn, "Bayesian Nonparametric Modeling for Causal Inference", In Journal of Computational and Graphical Statistics, vol. 20, Issue 1, Mar. 2011, 25 pages.

Huang, et al., "Scalable Hypergraph Learning and Processing", In Proceedings of IEEE International Conference on Data Mining, Nov. 14, 2015, 6 Pages.

Hudgens, et al., "Toward Causal Inference With Interference", In Journal of the American Statistical Association, vol. 103, Issue 482, Jun. 2008, 23 Pages.

Imai, et al., "Causal Inference with Interference and Noncompliance in Two-Stage Randomized Experiments", In Journal of the American Statistical Association, vol. 116, Issue 534, Jul. 2020, 13 Pages.

Jiang, et al., "Dynamic Hypergraph Neural Networks", In Proceedings of the Twenty-Eighth International Joint Conference on Artificial Intelligence, Aug. 10, 2019, pp. 2635-2641.

Kim, et al., "Reliable Estimation of Individual Treatment Effect with Causal Information Bottleneck", In Repository of arXiv:1906.03118v1, Jun. 7, 2019, 13 Pages.

Kipf, et al., "Semi-Supervised Classification with Graph Convolutional Networks", In Repository of arXiv:1609.02907v1, Sep. 9, 2016, 10 Pages.

Kohavi, et al., "Online Controlled Experiments at Large Scale", In Proceedings of the 19th ACM SIGKDD International Conference on Knowledge Discovery and Data Mining, Aug. 11, 2013, pp. 1168-1176.

Li, et al., "Link Prediction in Social Networks Based on Hypergraph", In Proceedings of the 22nd International Conference on World Wide Web, May 13, 2013, pp. 41-42.

Louizos, et al., "Causal Effect Inference with Deep Latent-Variable Models", In Proceedings of 31st International Conference in Advances on Neural Information Processing Systems, Dec. 4, 2017, 11 Pages.

Ma, et al., "Causal Inference Under Networked Interference and Intervention Policy Enhancement", In Proceedings of the 24th International Conference on Artificial Intelligence and Statistics, Apr. 13, 2021, 11 pages.

(56) References Cited

OTHER PUBLICATIONS

Mastrandrea, et al., "Contact Patterns in a High School: A Comparison Between Data Collected Using Wearable Sensors, Contact Diaries and Friendship Surveys", In Journal of PloS one, vol. 10, No. 9, Sep. 1, 2015, 26 Pages.

Morris, et al., "Weisfeiler and Leman Go Neural: Higher-Order Graph Neural Networks", In Proceedings of the AAAI Conference on Artificial Intelligence, vol. 33, Issue 01, Jul. 17, 2019, pp. 4602-4609.

Splawa-Neyman, et al., "On the Application of Probability Theory to Agricultural Experiments", In the Journal of Statistical Science, vol. 5, No. 4, Nov. 1990, 9 pages.

Ng, et al., "A Graph Autoencoder Approach to Causal Structure Learning", In Repository of arXiv:1911.07420v1, Nov. 18, 2019, 8 Pages.

Rakesh, et al., "Linked Causal Variational Autoencoder for Inferring Paired Spillover Effects", In Proceedings of the 27th ACM International Conference on Information and Knowledge Management, Oct. 22-26, 2018, pp. 1679-1682.

Rubin, Donald B., "Randomization Analysis of Experimental Data: The Fisher Randomization Test Comment", In Journal of the American Statistical Association, vol. 75, Issue 371, Sep. 1980, 4 pages.

Shalit, et al., "Estimating Individual Treatment Effect: Generalization Bounds and Algorithms", In Proceedings of the 34th International Conference on Machine Learning, Aug. 6, 2017, 10 Pages.

Sharma, Ankit, "Hypergraph Analytics: Modeling Higher-Order Structures and Probabilities", In Dissertation Submitted to the Faculty of Graduate School at University of Minnesota, May 2020, 268 Pages.

Sharma, et al., "Predicting Multi-Actor Collaborations using Hypergraphs", In Repository of arXiv:1401.6404v1, Jan. 24, 2014, 10 Pages.

Tchetgen, et al., "Auto-G-Computation of Causal Effects on a Network", In Journal of the American Statistical Association, vol. 116, Issue 534, Oct. 1, 2020, 30 Pages.

Tchetgen, et al., "On Causal Inference in the Presence of Interference", In Journal of Statistical methods in Medical Research, vol. 21, Issue 1, Nov. 10, 2010, 24 Pages.

Ugander, et al., "Graph Cluster Randomization: Network Exposure to Multiple Universes", In Proceedings of the 19th ACM SIGKDD International Conference on Knowledge Discovery and Data Mining, Aug. 11, 2013, 9 Pages.

Wan, et al., "Fine-Grained Spoiler Detection from Large-Scale Review Corpora", In Proceedings of the 57th Annual Meeting of the Association for Computational Linguistics, Jul. 28, 2019, pp. 2605-2610.

Wan, et al., "Item Recommendation on Monotonic Behavior Chains", In Proceedings of the 12th ACM Conference on Recommender Systems, Oct. 2-7, 2018, pp. 86-94.

Willmott,,"Advantages of the Mean Absolute Error (MAE) Over the Root Mean Square Error (RMSE) in Assessing Average Model Performance", In Journal of Climate Research, vol. 30, Issue 1, Dec. 19, 2005, pp. 79-82.

Xu, et al., "Hyperlink Prediction in Hypernetworks Using Latent Social Features", In Proceedings of 16th International Conference on Discovery Science, Oct. 6, 2013, pp. 324-339.

Yadati, et al., "HyperGCN: Hypergraph Convolutional Networks for Semi-Supervised Classification", In Repository of https://arxiv.org/pdf/1809.02589v1.pdf, Sep. 7, 2018, 12 Pages.

Annonymous Authors, et al., "Link Prediction in Hypergraphs Using Graph Convolutional Networks", In Proceedings of International Conference on Learning Representations (ICLR), Sep. 28, 2018, 13 Pages.

Yang, et al., "The Effects of Remote Work on Collaboration Among Information Workers", In Journal of Nature Human Behaviour, vol. 6, Jan. 2022, 14 Pages.

Ma, et al., "Causal Inference under Networked Interference and Intervention Policy Enhancement", In Repository of arXiv:2002.08506v2, May 4, 2021, 30 Pages.

"International Search Report Written Opinion Issued in PCT Patent Application No. PCT/US22/051114", dated Mar. 14, 2023, 14 Pages.

Zhao, et al., "FisrEbp: Enterprise Bankruptcy Prediction via Fusing its Intra-risk and Spillover-Risk", In Repository of arXiv:2202.03874v1, Feb. 1, 2022, 11 Pages.

* cited by examiner

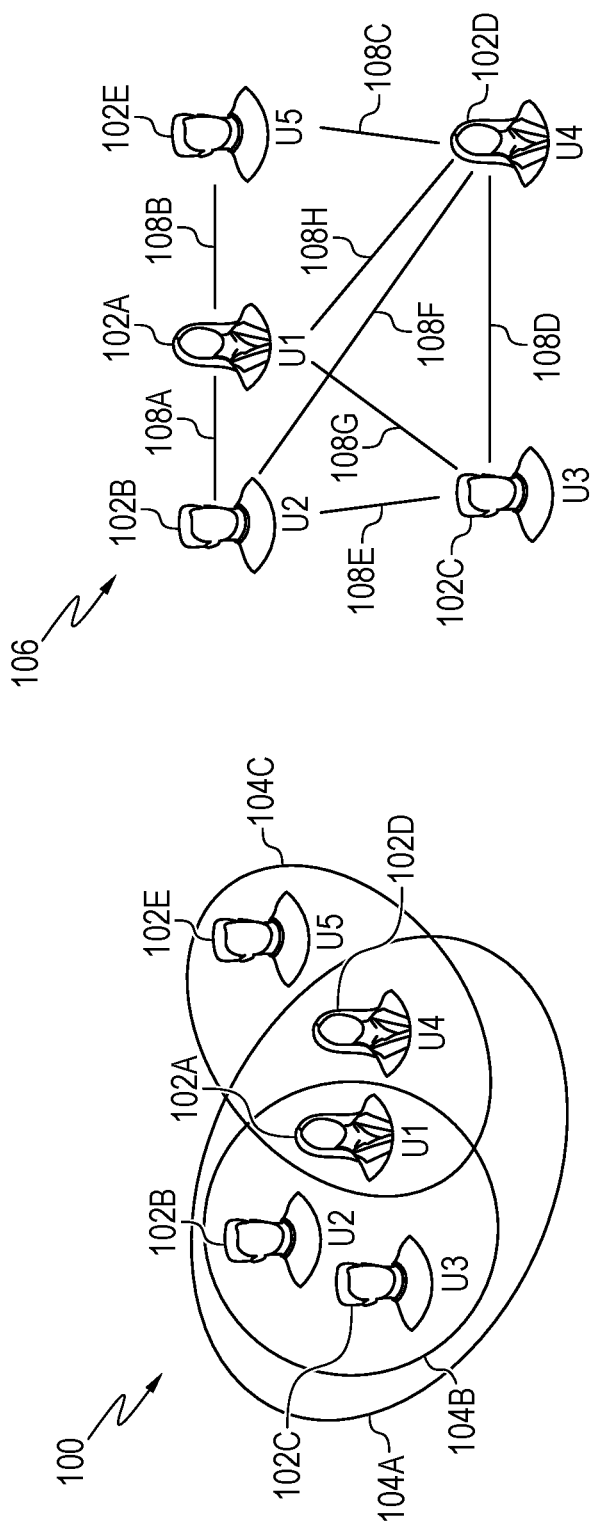
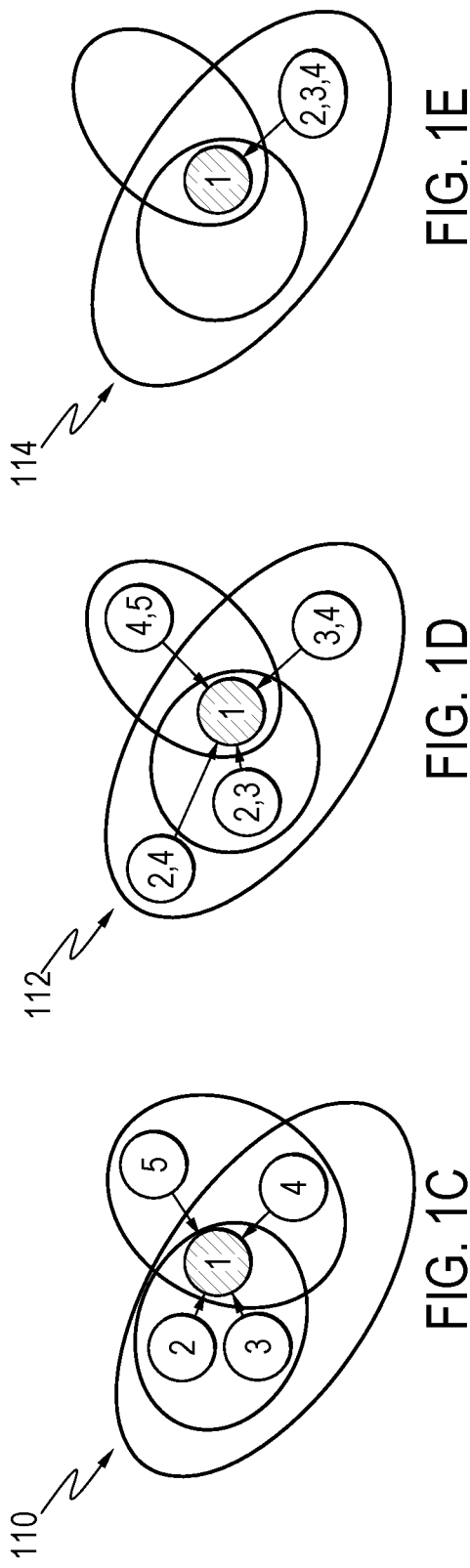

INDIVIDUAL TREATMENT EFFECT ESTIMATION UNDER HIGH-ORDER INTERFERENCE IN HYPERGRAPHS

BACKGROUND

The present disclosure relates to machine learning. In particular, the present disclosure relates to individual treatment effect (ITE) estimation under high-order interference in hypergraphs.

SUMMARY

The following presents a simplified summary in order to provide a basic understanding of some aspects described herein. This summary is not an extensive overview of the claimed subject matter. This summary is not intended to identify key or critical elements of the claimed subject matter nor delineate the scope of the claimed subject matter. This summary's sole purpose is to present some concepts of the claimed subject matter in a simplified form as a prelude to the more detailed description that is presented later.

In an embodiment described herein, a method for individual treatment effect (ITE) estimation under high-order interference in hypergraphs is described. The method is implemented in a computing system including a processor. The method includes accessing, via the processor, a hypergraph dataset including multi-way interactions among nodes within each hyperedge of a corresponding hypergraph, where the hypergraph dataset corresponds to a treatment assignment for each node. The method includes performing representation learning on the hypergraph dataset to control for confounders corresponding to features of each node and to learn a confounder representation for each node. The method also includes modeling a high-order interference representation for each node by propagating the learned confounder representation and the treatment assignment for each node with a hypergraph convolutional layer, while utilizing a hypergraph attention mechanism to assign an attention score to each node, where the attention score corresponds to a significance of interference for the corresponding node. The method further includes estimating the ITE for each node under the treatment assignment based on the learned confounder representation and the modeled high-order interference representation for each node.

In another embodiment, a computing system is described. The computing system includes a processor, a web-based application, and a communication connection for connecting remote computing systems to the computing system through a network, where each remote computing system corresponds to a user who engages in multi-way interactions using the web-based application. The computing system also includes a database for storing a hypergraph dataset including hypergraph data corresponding to the multi-way interactions between the users of the remote computing systems, where each user is represented as a node within the corresponding hypergraph. The computing system further includes a computer-readable storage medium operatively coupled to the processor. The computer-readable storage medium includes computer-executable instructions that, when executed by the processor, cause the processor to perform representation learning on the hypergraph dataset to control for confounders corresponding to features of each node and to learn a confounder representation for each node, as well as to model a high-order interference representation for each node by propagating the learned confounder representation and the treatment assignment for each node with a hypergraph convolutional layer, while utilizing a hypergraph attention mechanism to assign an attention score to each node, where the attention score corresponds to a significance of interference for the corresponding node. The computer-executable instructions, when executed by the processor, also cause the processor to estimate an ITE for each node under the treatment assignment based on the learned confounder representation and the modeled high-order interference representation for each node. The computer-executable instructions, when executed by the processor, also cause the processor to utilize the estimated ITE for each node to enhance a functionality of the web-based application with respect to the corresponding user.

In another embodiment, a computer-readable storage medium is described. The computer-readable storage medium includes computer-executable instructions that, when executed by a processor, cause the processor to access a hypergraph dataset including multi-way interactions among nodes within each hyperedge of a corresponding hypergraph, where the hypergraph dataset corresponds to a treatment assignment for each node, as well as to perform representation learning on the hypergraph dataset to control for confounders corresponding to features of each node and to learn a confounder representation for each node. The computer-executable instructions, when executed by the processor, also cause the processor to model a high-order interference representation for each node by propagating the learned confounder representation and the treatment assignment for each node with a hypergraph convolutional layer, while utilizing a hypergraph attention mechanism to assign an attention score to each node, where the attention score corresponds to a significance of interference for the corresponding node. The computer-executable instructions, when executed by the processor, also cause the processor to estimate an ITE for each node under the treatment assignment based on the learned confounder representation and the modeled high-order interference representation for each node.

The following description and the annexed drawings set forth in detail certain illustrative aspects of the claimed subject matter. These aspects are indicative, however, of a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

BRIEF DESCRIPTION OF THE DRAWINGS

The following detailed description may be better understood by referencing the accompanying drawings, which contain specific examples of numerous features of the disclosed subject matter.

FIG. 1A is a simplified schematic view of a portion of a hypergraph in which individuals are connected via group chats on a digital platform, with each group being represented as a hyperedge within the hypergraph;

FIG. 1B is a simplified schematic view of a portion of an ordinary graph in which each edge only connects exactly two individuals;

FIG. 1C is a schematic view showing an example of first-order interference;

FIG. 1D is a schematic view showing an example of second-order interference;

FIG. 1E is a schematic view showing an example of third-order interference;

DETAILED DESCRIPTION

Figure 2:
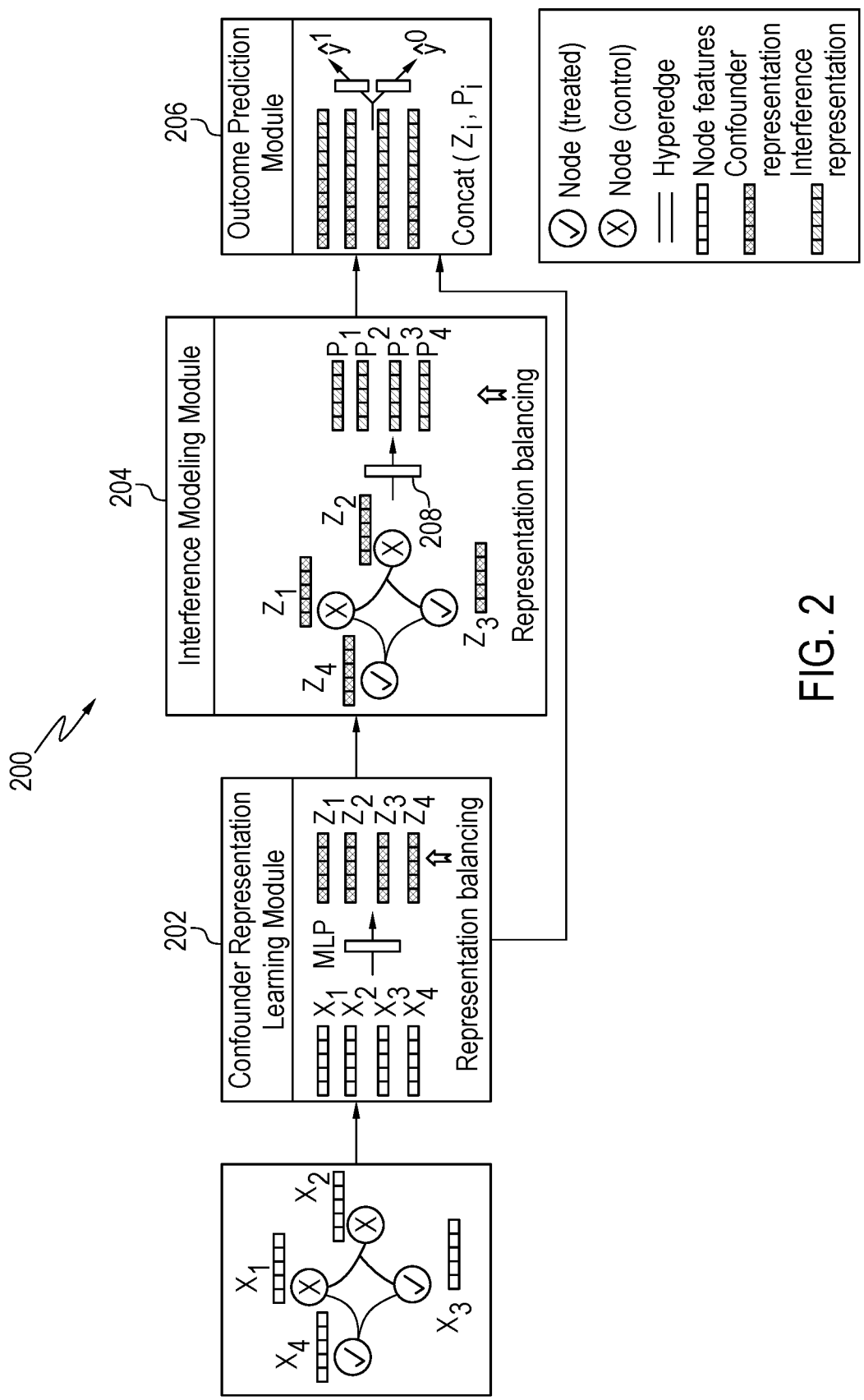
FIG. 2 is a schematic view depicting an exemplary embodiment of the framework for implementing the ITE estimation techniques described herein.

As a preliminary matter, some of the figures describe concepts in the context of one or more structural components, referred to as functionalities, modules, features, elements, etc. The various components shown in the figures can be implemented in any manner, for example, by software, hardware (e.g., discrete logic components, etc.), firmware, and so on, or any combination of these implementations. In one embodiment, the various components may reflect the use of corresponding components in an actual implementation. In other embodiments, any single component illustrated in the figures may be implemented by a number of actual components. The depiction of any two or more separate components in the figures may reflect different functions performed by a single actual component.

Other figures describe the concepts in flowchart form. In this form, certain operations are described as constituting distinct blocks performed in a certain order. Such implementations are exemplary and non-limiting. Certain blocks described herein can be grouped together and performed in a single operation, certain blocks can be broken apart into plural component blocks, and certain blocks can be performed in an order that differs from that which is illustrated herein, including a parallel manner of performing the blocks. The blocks shown in the flowcharts can be implemented by software, hardware, firmware, and the like, or any combination of these implementations. As used herein, hardware may include computing systems, discrete logic components, such as application specific integrated circuits (ASICs), and the like, as well as any combinations thereof.

Terminology

As for terminology, the phrase "configured to" encompasses any way that any kind of structural component can be constructed to perform an identified operation. The structural component can be configured to perform an operation using software, hardware, firmware and the like, or any combinations thereof. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware.

The term "logic" encompasses any functionality for performing a task. For instance, each operation illustrated in the flowcharts corresponds to logic for performing that operation. An operation can be performed using software, hardware, firmware, etc., or any combinations thereof.

As utilized herein, the terms "component," "system," "client," and the like are intended to refer to a computer-related entity, either hardware, software (e.g., in execution), and/or firmware, or a combination thereof. For example, a component can be a process running on a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any tangible, computer-readable storage medium.

Moreover, as used herein, the term "computer-readable storage medium" refers to an article of manufacture. In general, computer-readable storage media are used to host, store and/or reproduce computer-executable instructions and data for later retrieval and/or execution. When the computer-executable instructions that are hosted or stored on the computer-readable storage media are executed by a processor of a computing system, the execution thereof causes, configures and/or adapts the executing computing system to carry out various steps, processes, routines, methods and/or functionalities, including the steps, processes, routines, methods, and/or functionalities described herein. Examples of computer-readable storage media include, but are not limited to, optical storage media (such as Blu-ray discs, digital video discs (DVDs), compact discs (CDs), optical disc cartridges, and the like), magnetic storage media (such as hard disk drives, floppy disks, magnetic tape, and the like), memory storage devices (such as random access memory (RAM), read-only memory (ROM), memory cards, thumb drives, and the like), and cloud storage (such as online storage services). Computer-readable storage media may deliver computer-executable instructions to a computing system for execution via various transmission means and mediums, including carrier waves and/or propagated signals. However, for purposes of this disclosure, the term "computer-readable storage medium (or media)" refers specifically to non-transitory forms of computer-readable storage media and expressly excludes carrier waves and/or propagated signals.

As used herein, the term "causal inference" refers generally to the process of inferring causality from data. Stated another way, "causal inference" refers generally to the process of determining the independent, actual effect of a certain phenomenon that is occurring within a larger system.

As used herein, term "confounder" refers to a variable whose presence affects both the treatment and the outcome so that the results may not reflect the actual relationship between the treatment and the outcome. This occurs as a result of the confounder correlating (either positively or negatively) with both the treatment and the outcome. The existence of confounders is one quantitative reason why correlation does not necessarily imply causation. Relatedly, the term "unconfoundedness" refers loosely to the concept that all the variables affecting the treatment and the outcome are observed and can be controlled for.

Generally speaking, the term "covariate" refers to a control variable that is observed rather than manipulated. As an example, for embodiments in which each node corresponds to a person or individual, the covariates may correspond to various characteristics of such people.

As used herein, the term "individual treatment effect (ITE)" refers to the causal effect of a particular treatment on the outcome of a specific unit (e.g., specific individual or group). Stated another way, ITE refers to the difference between two potential outcomes for a specific unit (e.g., the value of the outcome when the unit is treated versus the value of the outcome when the unit is not treated).

As used herein, the term "hypergraph" refers to a graph in which each edge (referred to as a "hyperedge") can join or connect any number of vertices or nodes (referred to as "hypervertices" or "hypernodes"). This is in contrast to an ordinary graph, in which each edge joins or connects exactly two vertices or nodes.

Generally speaking, the term "spillover effect" refers to the concept of one unit's outcome being influenced by the treatment of one or more other units.

Overview of Technical Problem and ITE Estimation Techniques Described Herein

Group interactions among individuals exist in a wide range of web-based platforms, e.g., day-to-day group chats on social media applications, workplace interactions on communication platforms, and group communications on online forums. Although the conventional pairwise graph definition covers a vast number of applications (e.g., person-to-person social networks), it fails to capture the complete information for these group interactions for cases in which each interaction may involve more than two individuals. Therefore, according to embodiments described herein, hypergraph-based techniques are used to address this limitation.

FIGS. 1A-E are simplified schematic views depicting the differences between hypergraphs and ordinary graphs, as well as the differences between varying levels of interference within such graphs. Specifically, FIG. 1A is a simplified schematic view of a portion of a hypergraph 100 in which individuals (or nodes) 102A-E are connected via group chats on a digital platform or web-based application, with each group being represented as a hyperedge 104A-C within the hypergraph 100. As shown in FIG. 1A, each hyperedge 104A-C connects an arbitrary number of individuals 102A-E. In contrast, FIG. 1B is a simplified schematic view of a portion of an ordinary graph 106 in which each edge 108A-H only connects exactly two individuals (or nodes) 102A-E.

While studies have been devoted to utilizing such a generalized hypergraph structure to facilitate machine learning tasks, the majority were still executed at the statistical correlation level, e.g., predicting a user' product purchase interests by capturing the correlations between the user's profile (node features), group chat memberships (hypergraph structure), and historical purchase behavior (node labels). A critical limitation here is the lack of causality, which is particularly important for understanding the impact of a policy intervention (e.g., advertisement placement) or a product feature change on web-based applications. For individuals connected as in FIG. 1A, a marketer may ask, for example, the manner in which showing an advertisement to each individual (e.g., a particular "treatment" of the individual) would causally influence their conversion outcome (e.g., product purchase). Such a causal inference task requires constructing the counterfactual state of the same individual by holding all other possible factors constant except the treatment variable of interest. This is a particularly difficult problem on hypergraph data since the outcome of each individual is impacted, not only by their own confounding factors (e.g., each individual's demographic information), but also by interference from other individuals in the hypergraph (e.g., advertisement placements for other individuals who may pass the promotional information to the target individual through group chats, for example).

Accordingly, the techniques described herein relate to learning causal effects on hypergraphs. More specifically, the techniques described herein relate to utilizing observational data to estimate individual treatment effect (ITE) in the presence of hypergraph interference. Such techniques are motivated, at least in part, by several deficiencies in current approaches, such as, in particular, deficiencies resulting from the empirical constraints of randomized experiments and the inability to determine high-order interference on hypergraphs.

With respect to deficiencies resulting from the empirical constraints of randomized experiments, the utilization of randomized controlled trials (RCTs) is currently one of the most reliable approaches for treatment effect estimation. However, running RCTs is often expensive and impractical, and RCTs are especially difficult on graphs due to the dependencies among connected nodes.

With respect to deficiencies resulting from the inability to determine high-order interference on hypergraphs, the present techniques relate to ITE estimation, which aims to estimate the causal effect of a certain treatment (e.g., advertisement placement) on an outcome (e.g., conversion rate) for each individual/node. Classic ITE estimation is based on the Stable Unit Treatment Value (SUTVA) assumption, which is that there is no interference among instances or, in other words, that the spillover effect is not present. Under that assumption, the potential outcomes for any instance are not influenced by the treatment assignment of other instances. This assumption is generally inaccurate for real-world data, thus resulting in biased causal effect estimations, especially on graph-structured data where interference among instances is ubiquitous. An increasing amount of efforts have been aimed at addressing this problem; however, most approaches assume that the interference only exists in a pairwise way on ordinary graphs (as shown in FIG. 1B). This pairwise interference notion is insufficient to characterize the high-order interference that exists on hypergraphs. As an example, FIG. 1C is a schematic view showing an example of first-order interference 110; FIG. 1D is a schematic view showing an example of second-order interference 112; and FIG. 1E is a schematic view showing an example of third-order interference 114. As shown in the figures, within a group chat (hyperedge) between $u_1$, $u_2$ and $u_3$, an individual's ($u_1$) conversion outcome can be affected by the first-order interference from other individuals ($u_2 \rightarrow u_1$ and $u_3 \rightarrow u_1$), as well as the high-order interference from the interactions among other individuals (e.g., the interaction between $u_2$ and $u_3$ may also influence the exposure of the promotion information to $u_1$; consequently, $u_1$'s conversion rate can be affected by this second-order interaction effect, i.e., $u_2 \times u_3 \rightarrow u_1$). Notice that the number of such high-order interference items grows combinatorially as the size of a hyperedge increases, leading to a significant information gap between the original hypergraph and the projected pairwise ordinary graph (which accounts for first-order interference only). As a result, there is a need for techniques that are capable of modeling high-order interference.

The techniques described herein solve this problem by providing systems and methods for ITE estimation under high-order interference in hypergraphs. Such ITE estimation techniques are accomplished using a novel framework, which is referred to herein as "Causal Inference under Spillover Effects in Hypergraphs," abbreviated as "Hyper-SCI." At a high-level, the techniques described herein control for the confounders and model high-order interference based on representation learning. Such techniques then estimate the outcomes based on the learned representations. More specifically, the techniques described herein provide for the following: (1) confounder control; (2) high-order interference modeling; and (3) outcome prediction.

First, with respect to confounder control, the present techniques are based on the widely-accepted unconfoundedness assumption, which states that the confounders are contained in the observed features. With this assumption, the present techniques leverage representation learning techniques to capture and control for confounders from the features of each individual/node. Note, however, that the discrepancy between confounder distributions in the treatment group and the control group can lead to biases in causal effect estimations. Therefore, the present techniques utilize a representation balancing technique to mitigate the discrepancy between these two distributions.

Second, with respect to modeling high-order interference, such modeling can be challenging due to the complexity of enumerating multi-way interactions among nodes within each hyperedge. Historically, the original hypergraph was simplified and approximated through a series of projected ordinary graphs. However, the present techniques utilize hypergraph neural networks to model interference by learning interference representations for each node. Specifically, to learn the interference representations, the learned confounder representations and the treatment assignment are propagated via hypergraph convolutional layer and attention operations.

Finally, with respect to outcome prediction, the present techniques utilize the learned representations of confounders and interference to predict/estimate the potential outcomes corresponding to the treatment assignment for each node. In this manner, the present techniques enable ITE estimation for hypergraphs in which high-order interference is prevalent.

Formal Problem Definition and Analysis for ITE Estimation Techniques Described Herein This section provides a formal problem definition and a brief analysis for the ITE estimation techniques described herein. As a preliminary matter, Table 1 provides a listing of notations that are used herein.

TABLE 1

| Notation | Definition |
| --- | --- |
| $\mathcal{H}$ | Hypergraph |
| $\mathcal{V}, \varepsilon$ | Set of nodes/hyperedges |
| H | Hypergraph structure matrix |
| n | Number of nodes |
| m | Number of hyperedges |
| $\mathcal{N}_i$ | Set of neighboring nodes for the i-th node |
| $\mathcal{N}_e$ | Set of nodes on the hyperedge e |
| X, $x_i$ | Features of all nodes/the i-th node |
| T, $t_i$ | Treatment assignment of all nodes/the i-th node |
| Y, $y_i$ | Observed outcome of all nodes/the i-th node |
| $y_i^1, y_i^0$ | Potential outcomes of the i-th node |
| $\Phi_Y(\cdot)$ | Potential outcome function |
| $\tau_i, \hat{\tau}_i$ | True/Predicted ITE for the i-th node |
| $y_i, \hat{y}_i$ | True/Predicted outcome for the i-th node |
| $(\cdot)_{-i}$ | Variables for all the nodes except for the i-th node |
| $\delta_i$ | Spillover effect of the i-th node |
| SMR ($\cdot$) | Summary function |
| O, $o_i$ | Environment information for the i-th node |
| Z, $z_i$ | Confounder representation of all nodes/the i-th node |
| $\Psi(\cdot)$ | Interference representation learner |
| $f_1(\cdot), f_0(\cdot)$ | Potential outcome prediction functions |
| P, $p_i$ | Interference representations of all nodes/the i-th node |
| r (i) | Ratio of treatment assignment of the i-th node in its neighborhood |

Turning now to the formal problem definition, the following definition is referred to as Definition 1: "Suppose a set of individuals $\mathcal{V} = \{v_i\}_{j=1}^n$ are connected via hyperedges $\varepsilon = \{e_k\}_{k=1}^m$; together these form a hypergraph $\mathcal{H} = \{\mathcal{V}, \varepsilon\}$ with n nodes and m hyperedges, where each hyperedge can connect an arbitrary number of nodes." The observational data on this hypergraph can be denoted as $\{X, \mathcal{H}, T, Y\}$, where $X = \{x_i\}_{i=1}^n$, $T = \{t_i\}_{i=1}^n$ and $Y = \{y_i\}_{i=1}^n$ represent node features, treatment assignments, and observed outcomes, respectively. The term $H = \{h_{i,e}\} \in \mathbb{R}^{n \times m}$ is an incidence matrix which describes the hypergraph structure of $\mathcal{H}$. The term $h_{i,e} = 1$ if node i is in hyperedge e; otherwise $h_{i,e} = 0$. For ease of discussion, the treatment assignment is treated as a binary variable (i.e., $t_i \in \{0, 1\}$). However, the definition can also be extended to non-binary categorical variables and continuous variables.

The following definition is referred to as Definition 2: "The potential outcome of the instance i (denoted by $y_i^1$ or $y_i^0$) is defined as the realized value of outcome for instance i under the treatment value $t_i = 1$ or $t_i = 0$. These potential outcomes can be instantiated via a transformation $Y_i^{T_i} = \Phi_Y(T_i, X_i, T_{-i}, X_{-i}, H)$. The function $\Phi_Y$ can be regarded as a (non-deterministic) function to output potential outcomes, which takes each node's treatment assignment, node features, the information (e.g., treatment assignment and node features) of other nodes on the hypergraph, and the hypergraph structure as input, i.e., $y_i^{t_i} = \Phi_Y(t_i, x_i, T_{-i}, X_{-i}, H)$, where the subscript –i denotes all other nodes on $\mathcal{H}$ except i."

Given the above preliminary definitions, the formal definition of individual treatment effect on hypergraphs can then be provided as Definition 3: "For each node i on the hypergraph $\mathcal{H}$, the individual treatment effect (ITE) is defined by the difference between potential outcomes corresponding to $t_i=1$ and $t_i=0$, as shown in Equation (1)."

$$\tau(x_i, T_{-i}, X_{-i}, H) \quad (1)$$
$$= \mathbb{E}\left[Y_i^1 - Y_i^0 | X_i = x_i, T_{-i} = T_{-i}, X_{-i} = X_{-i}, H = H\right]$$
$$= \mathbb{E}[\Phi_Y(1, x_i, T_{-i}, X_{-i}, H) - \Phi_Y(0, x_i, T_{-i}, X_{-i}, H)]$$

Meanwhile, the notion of spillover effect is introduced as shown in the following Definition 4 to assess the level of interference on hypergraphs: "The spillover effect of node i under its treatment $t_i$ and other nodes' treatment assignment $T_{-i}$ on the hypergraph $\mathcal{H}$ is defined as shown in Equation (2)."

$$\delta_i = \mathbb{E}[\Phi_Y(t_i, x_i, T_{-i}, X_{-i}, H) - \Phi_Y(t_i, x_i, 0, X_{-i}, H)] \quad (2)$$

According to embodiments described herein, given the observed data {X, $\mathcal{H}$, T, Y}, ITE (as defined by Equation 1) is estimated for each node in $\mathcal{H}$, while accounting for the existence of high-order interference (as defined by Equation 2).

With the above definitions, the individual treatment effect can be estimated from the observational data under two assumptions. First, for each node, it is assumed that there exists a summary function capable of characterizing all the environmental information related to this node on the hypergraph. Suppose there is a summary function SMR(•). For each node i, SMR(•) takes the hypergraph structure H, the treatment assignment of other nodes $T_{-i}$ and the features of these nodes $X_{-i}$ as input, then maps them into a vector $o_i$, as provided by Equation (3).

$$o_i = SMR(H, T_{-i}, X_{-i}) \quad (3)$$

In Equation (3), the term (H, X, T) denotes the random variables for the hypergraph structure, features, and treatment assignment, respectively, for any node. Assumption 1 (referred to herein as the "Expressiveness of Summary Function Assumption") can then be formalized as follows: "For any node i and any values of H, $X_{-i}$, and $T_{-i}$, if the output of summary function $o_i$ is determined, then the value of the potential outcomes $y_i^1$ and $y_i^0$ with feature $x_i$ are also determined."

The second assumption then extends the unconfoundedness assumption to the hypergraph interference setting. In other words, it assumes that, conditioned on the above summary function, the observed features can capture all possible confounders. Assumption 2 (referred to herein as the "Unconfoundedness Assumption") can then be formalized as follows: "For any node i, given the node features, the potential outcomes are independent with the treatment assignment and summary of neighbors, i.e., $Y_i^1, Y_i^0, \perp\!\!\!\perp, T_i, O_i | X_i$."

Based on the above assumptions, the identification of potential outcomes $Y_i^1$ and $Y_i^0$ for each node i can be proved (here $Y_i^1$ is taken as an example), as provided by Equations (4)-(9).

$$\mathbb{E}\left[Y_i^1 | T_i = 1, X_i = x_i, T_{-i} = T_{-i}, X_{-i} = X_{-i}, H = H\right] \quad (4)$$
$$= \mathbb{E}[\Phi_Y(T_i = 1, X_i = x_i, T_{-i} = T_{-i}, X_{-i} = X_{-i}, H = H)] \quad (5)$$

-continued
$$= \mathbb{E}[\Phi_Y(T_i = 1, X_i = x_i, O_i = o_i)] \quad (6)$$
$$= \mathbb{E}[\Phi_Y(T_i = 1, X_i = x_i, O_i = o_i) | X_i = x_i] \quad (7)$$
$$= \mathbb{E}[\Phi_Y(T_i = 1, X_i = x_i, O_i = o_i) | X_i = x_i, T_i = 1, O_i = o_i] \quad (8)$$
$$= \mathbb{E}[Y_i | X_i = x_i, T_i = 1, O_i = o_i] \quad (9)$$

Here, Equations (4) and (5) are based on the definition of potential outcome in this setting; Equation (6) is inferred from Assumption 1; Equation (7) is a straightforward derivation; Equation (8) is based on Assumption 2; and Equation (9) is based on the widely-used consistency assumption. Based on the above proof for the identification of potential outcomes, the estimation of ITE can then be straightforwardly derived.

Exemplary Framework for ITE Estimation Under High-Order Interference in Hypergraphs Based on the problem definition and analysis described in the previous section, the present techniques provide a neural-network-based framework, HyperSCI, that enables ITE estimation under high-order interference on hypergraphs. As an example, FIG. 2 is a schematic view depicting an exemplary embodiment of the framework 200 for implementing the ITE estimation techniques described herein. This framework 200 includes three components: a confounder representation learning module 202, an interference modeling module 204, and an outcome prediction module 206. Holistically, the goal is to learn an expressive transformation to summarize high-order interferences (e.g., based on Assumption 1) and then to use the interference representation, the confounder representation, and the treatment assignment to estimate the expected potential outcome (e.g., based on Assumption 2).

Turning now to a description of the confounder representation learning module 202, the node features $x_i$ are first encoded into a latent space via a multilayer perceptron (MLP) module, i.e., $z_i = MLP(x_i)$. This results in a set of representations $Z = \{z_i\}_{i=1}^n$, which is expected to capture all potential confounders, so the model can mitigate the confounding biases by controlling for the learned representation $z_i$.

However, note that a discrepancy may exist between the distributions of confounder representation Z in the treatment group and the control group, incurring biases in causal effect estimation. To minimize such a discrepancy, representation balancing techniques are leveraged by adding a discrepancy penalty to the loss function, where this discrepancy penalty can be calculated with any suitable distribution distance metric. For example, in some embodiments, the Wasserstein-1 distance between the representation distributions of the treatment group and the control group is utilized as the distribution distance metric.

Figure 3:
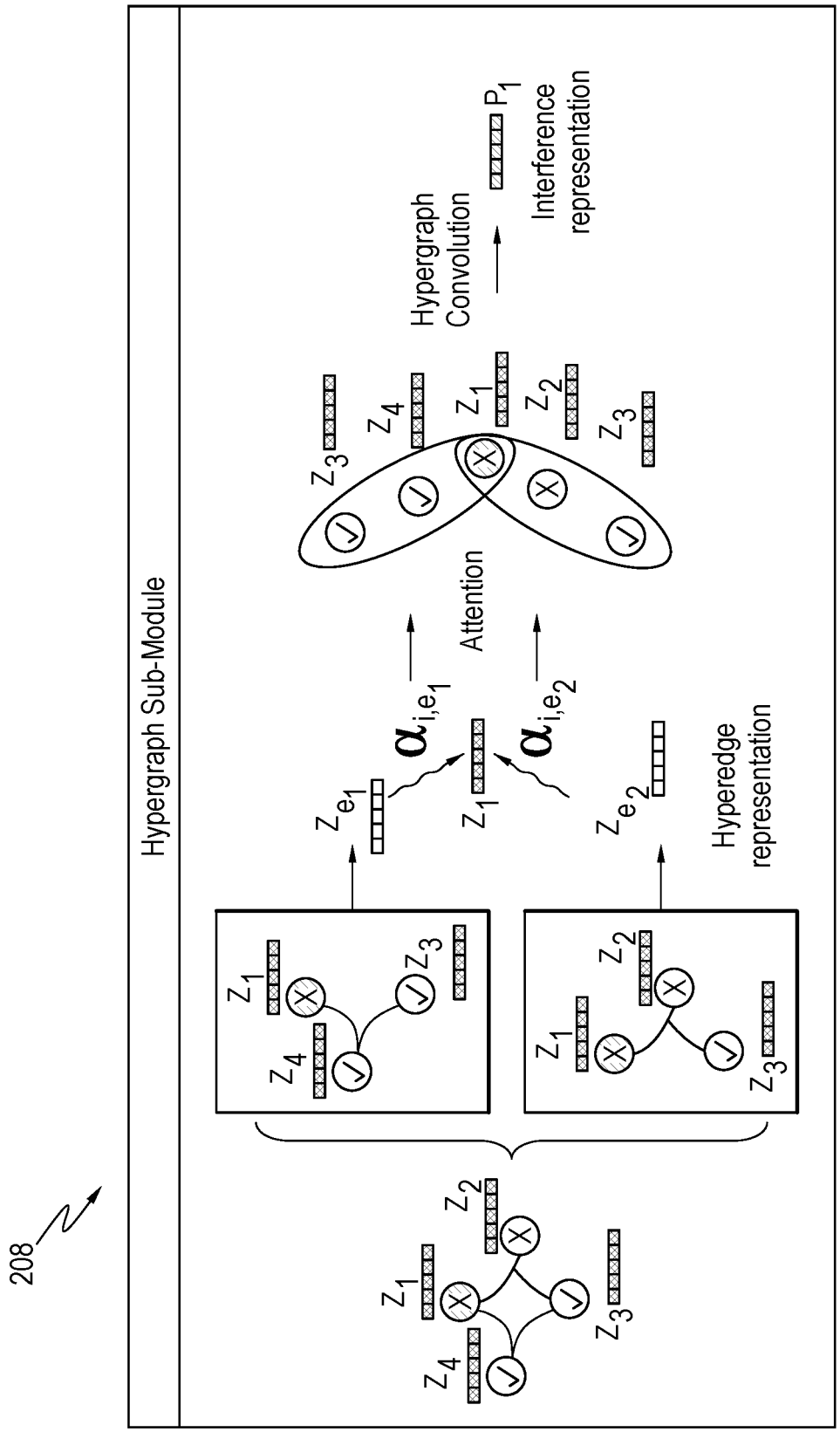
FIG. 3 is a schematic view depicting an exemplary embodiment of the hypergraph sub-module described with respect to the framework of FIG. 2.

With regard to the interference modeling module 204, the confounder representation (Z), the treatment assignment (T), and the relational information on the hypergraph (H={$h_{i,e}$}) are taken as input and are used to capture the high-order interference for each node. More specifically, a transformation function $\psi(\cdot)$ is learned using a hypergraph sub-module 208 to generate the interference representations ($p_i$) for each node i, i.e., $p_i = \psi(Z, H, T_{-i}, t_i)$. FIG. 3 is a schematic view depicting an exemplary embodiment of the hypergraph sub-module 208. As shown in FIG. 3, the hypergraph sub-module 208 is implemented with a hypergraph convolutional network and a hypergraph attention mechanism, where the convolutional operator forms the skeleton of interference from hyperedges, and the attention operator enhances this mechanism by allowing flexible node contributions to each hyperedge.

To learn the interference representations that encode the interference in the hypergraph for each node, the treatment assignment and confounder representations are propagated with a hypergraph convolutional layer. A vanilla Laplacian matrix is first introduced for the hypergraph $\mathcal{H}$, as shown in Equation (10).

$$L=D^{-1/2}HB^{-1}H^TD^{-1/2} \quad (10)$$

Here, $D \in \mathbb{R}^{n \times n}$ is a diagonal matrix, where each element represents the node degree (i.e., $\Sigma_{e=1}^{m} h_{i,e}$). In addition, $B \in \mathbb{R}^{m \times m}$ is another diagonal matrix, where each element represents the size of each hyperedge ($\Sigma_{i=1}^{n} h_{i,e}$). The hypergraph convolutional operator may then be defined according to Equation (11).

$$p^{(l+1)}=\text{LeakyReLU}(LP^{(l)}W^{(l+1)}) \quad (11)$$

In Equation (11), $p^{(l)}$ represents the representations from the l-th layer in the hypergraph sub-module 208. The first layer is fed with the previous confounder representation masked by the treatment assignment, i.e., $p_i^{(0)}=t_i*z_i$, where * denotes element-wise multiplication. Moreover, $W^{(l+1)} \in \mathbb{R}^{d^{(l)} \times d^{(l+1)}}$ is the parameter matrix in the (l+1)-th layer, where $d^{(l)}$ and $d^{(l+1)}$ refer to the dimensionality of the interference representations in the l-th and (l+1)-th layers, respectively.

Although the above convolutional layer can pass interferences through hyperedges, it does not provide much flexibility to account for the significance of interference for different nodes through different hyperedges. For instance, in the aforementioned online advertising example, intuitively, those individuals who are active in certain group chats are more likely to influence or be influenced by others in these groups. To better capture this intrinsic relationship between nodes and hyperedges on a hypergraph, a hypergraph attention mechanism is leveraged to learn attention weights for each node and the corresponding hyperedges that contain each node.

More specifically, a representation is computed for each hyperedge (e) by aggregating across its associated nodes ($\mathcal{N}_e$): $z_e=\text{AGG}(\{z_i | i \in \mathcal{N}_e\})$. Here, AGG(•) can be any suitable aggregation function (e.g., the mean aggregation). For each node i and its associated hyperedge e, the attention score between a node i and a hyperedge e can be calculated as provided by Equation (12).

$$a_{i,e} = \frac{\exp(\sigma(\text{sim}(z_iW_a, z_eW_a)))}{\sum_{k \in \varepsilon_i} \exp(\sigma(\text{sim}(z_iW_a, z_kW_a))} \quad (12)$$

In Equation (12), σ(•) denotes a non-linear activation function, and $\varepsilon_i$ denotes the set of hyperedges associated with the node i. Here, the term $W_a$ is used to denote a parameter matrix to compute the node-hyperedge attention. In addition, sim(•) is a similarity function, which can be implemented as provided by Equation (13).

$$\text{sim}(x_i,x_j)=a^T[x_i \| x_j] \quad (13)$$

In Equation (13), a is a weight vector, and [•‖•] is a concatenation operation.

The attention scores are then used to model the interference with different significance. Specifically, the original incidence matrix H in Equation (10) is replaced with an enhanced matrix $\tilde{H}=\{\tilde{h}_{i,e}\}$ where $\tilde{h}_{i,e}=\alpha_{i,e}h_{i,e}$. In this way, the interference from different nodes on the same hyperedge can be assigned with different importance weights, indicating different levels of contribution for interference modeling. The final representations from the last convolutional layer are denoted as $P=\{p_i\}_{i=1}^{n}$. Such final representations capture the high-order interference for each node.

Moreover, similarly to the confounder representation learning module 202, the interference modeling module 204 may utilize representation balancing techniques to calculate a discrepancy penalty to reflect the difference between the distributions of interference representations in the treatment group and the control group. These two discrepancy penalties may then be summarized/combined to compute a representation balancing loss, denoted by $\mathcal{L}_b$.

With respect to the outcome prediction module 206, the potential outcomes may be modeled using the confounder representation $z_i$ and the interference representation $p_i$, as provided by Equation (14).

$$\hat{y}_i^1=f_1([z_i \| p_i])\hat{y}_i^0=f_0([z_i \| p_i]) \quad (14)$$

In Equation (14), $f_1(•)$ and $f_0(•)$ are learnable functions to predict the potential outcome with respect to t=1 and t=0. In addition, $f_1(•)$ and $f_0(•)$ are implemented with two MLP modules. The prediction for the observed outcome is then obtained by $\hat{y}_i=\hat{y}_i^{t_i}$. The model is optimized to minimize the loss function shown in Equation (15).

$$\mathcal{L}=\Sigma_{i=1}^{n}(y_i-\hat{y}_i)^2+\alpha\mathcal{L}_b+\lambda\|\Theta\|^2 \quad (15)$$

In Equation (15), the first term is the standard mean squared error; $\mathcal{L}_b$ is the representation balancing loss; and Θ represents the parameters in this neural network model. In addition, a and are two hyperparameters that control the weights for the representation balancing loss and the parameter regularization term. The ITE for each instance i can then be estimated as $\hat{\tau}_i=\hat{y}_i^1-\hat{y}_i^0$.

It should be noted that the framework 200 described with respect to FIGS. 2 and 3 is provided for exemplary purposes only. In practice, the ITE estimation techniques described herein may be implemented using any suitable variation or extension of this framework, depending on the details of the particular implementation.

Figure 4:
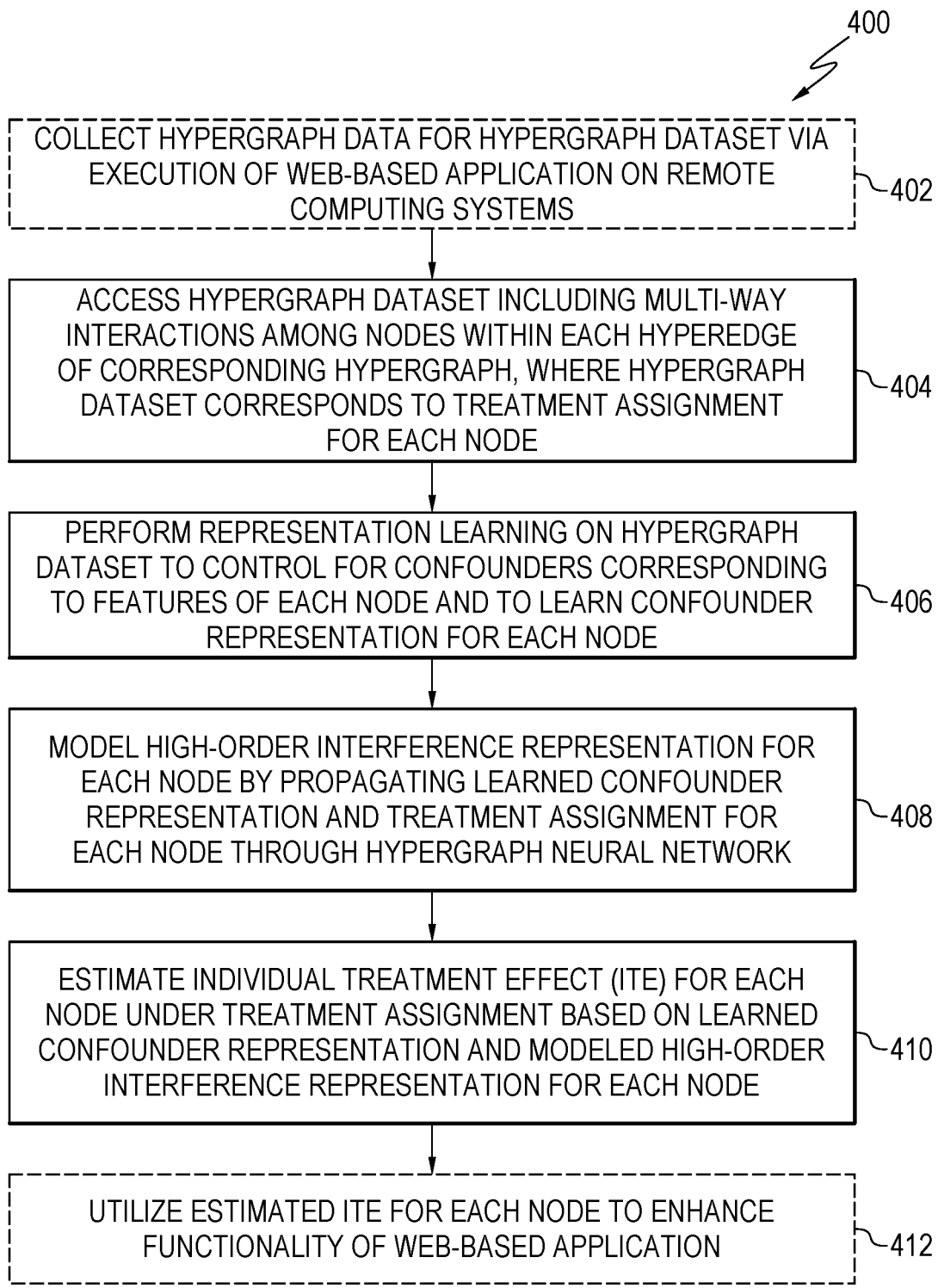
FIG. 4 is a process flow diagram of a method for individual treatment effect (ITE) estimation under high-order interference in hypergraphs according to embodiments described herein.

Exemplary Method for ITE Estimation Under High-Order Interference in Hypergraphs FIG. 4 is a process flow diagram of a method 400 for ITE estimation under high-order interference in hypergraphs according to embodiments described herein. The method 400 is executed via a computing system, such as the computing system described with respect to FIG. 5. The computing system includes one or more processors and one or more computer-readable storage media including computer-executable instructions that, when executed by the processor(s), cause the processor(s) to perform the blocks of the method 400. In addition, in some exemplary embodiments, the method 400 is executed within the context of a network environment including one or more web-based application provider computing systems and any number of remote user computing systems that execute the web-based application(s), as described further with respect to the exemplary network environment of FIG. 6.

The method 400 may begin at optional block 402, at which hypergraph data for a hypergraph dataset are collected via execution of a web-based application on multiple remote computing systems. In various embodiments, the computing system/server implementing the method 400 provides for execution of the web-based application on the remote computing systems via the network, as described herein. Moreover, in various embodiments, the web-based application includes a social media application, a communication application, a calendar application, a professional networking application, an employee experience application, a health application, a fitness application, or any other application that involves interactions between three or more users (or, in some cases, interactions between three or more items or other entities).

At block 404, the hypergraph dataset, which accounts for multi-way interactions among nodes (e.g., users) within each hyperedge of the corresponding hypergraph and includes a treatment assignment for each node, is accessed by the processor(s) of the computing system implementing the method 400. A t block 406, representation learning is performed on the hypergraph dataset to control for confounders corresponding to features of each node and to learn a confounder representation for each node. In various embodiments, this includes encoding the features of the nodes into a latent space using an MLP technique, resulting in a set of confounder representations for the nodes that capture potential confounders. In addition, in some embodiments, this includes performing representation balancing on the learned confounder representations to mitigate discrepancies between distributions of the learned confounder representations, e.g., discrepancies between the confounder representation distribution for the control group and the confounder representation distribution for the treatment group.

At block 408, a high-order interference representation is modeled for each node by propagating the learned confounder representation and the treatment assignment for each node through a hypergraph neural network. More specifically, according to embodiments described herein, this includes propagating the learned confounder representation and the treatment assignment for each node with a hypergraph convolutional layer, while utilizing a hypergraph attention mechanism to assign an attention score to each node, where the attention score corresponds to a significance of interference for the corresponding node. In addition, in some embodiments, this includes performing representation balancing on the modeled high-order interference representations to mitigate discrepancies between distributions of the modeled high-order interference representations, e.g., discrepancies between the high-order interference representation distribution for the control group and the high-order interference representation distribution for the treatment group.

At block 410, an ITE is estimated for each node under the treatment assignment based on the learned confounder representation and the modeled high-order interference representation for each node. Furthermore, at optional block 412, the estimated ITE for each node may be utilized to enhance the functionality of the web-based application. As an example, in some embodiments, the estimated ITE for each node is utilized to calculate a user-specific parameter for the web-based application, and one or more features of the web-based application are then personalized with respect to the corresponding user based on the calculated user-specific parameter. For example, personalizing the feature(s) of the web-based application may include automatically tailoring advertisements and/or recommendations to the corresponding user. As another example, in some embodiments, the estimated ITE for each node is utilized to calculate a parameter corresponding to the multi-way interactions between the users, and the functionality of the web-based application is then modified to optimize the parameter. For example, in such embodiments, the calculated parameter may be a generalized parameter relating to the functionality of the web-based application across multiple remote computing systems (as evidenced by the interactions between multiple users), and one or more aspects of the web-based application may be modified to effect an improvement in the functionality corresponding to such parameter. As yet another example, for embodiments in which the remote computing systems include wearable computing systems with integrated sensors, the estimated ITE for each node may be utilized to calculate a parameter corresponding to behaviors and/or characteristics of the users wearing the computing systems, and this information may then be used to update one or more aspects of the web-based application and/or to modify the functionality of the web-based application with respect to particular users. For example, in such embodiments, updating the aspect(s) of the web-based application may include completing a study corresponding to the behaviors and/or characteristics of the users. Moreover, those skilled in the art will appreciate that the embodiments described herein can also be extended to applications involving multi-way interactions between items, objects, and/or other entities, rather than users. For example, such embodiments can be used to analyze the relationships between various items that are for sale within the context of a web-based application that provides retail sales services (e.g., to analyze the manner in which the purchase of one item affects the purchase of one or more other related items), and/or to analyze the relationships between media content within the context of a web-based application that provides streaming services (e.g., to analyze the manner in which the viewership of one video affects the viewership of one or more other related videos). Furthermore, in response to such analysis, the corresponding web-based application may then be optimized in various ways, such as, for example, by linking related items or media content together in terms of advertisements, recommendations, and the like.

The block diagram of FIG. 4 is not intended to indicate that the blocks of the method 400 are to be executed in any particular order, or that all of the blocks of the method 400 are to be included in every case. Moreover, any number of additional blocks may be included within the method 400, depending on the details of the specific implementation. For example, in some embodiments, the method 400 also includes utilizing the estimated ITE for each node for any number of other applications, such as to facilitate one or more studies relating to complex interactions between multiple individuals, animals, items, or the like. Generally speaking, the ITE estimation techniques described herein may be utilized for any suitable types of hypergraph applications and are not limited to applications involving interactions between users of computing systems.

Figure 5:
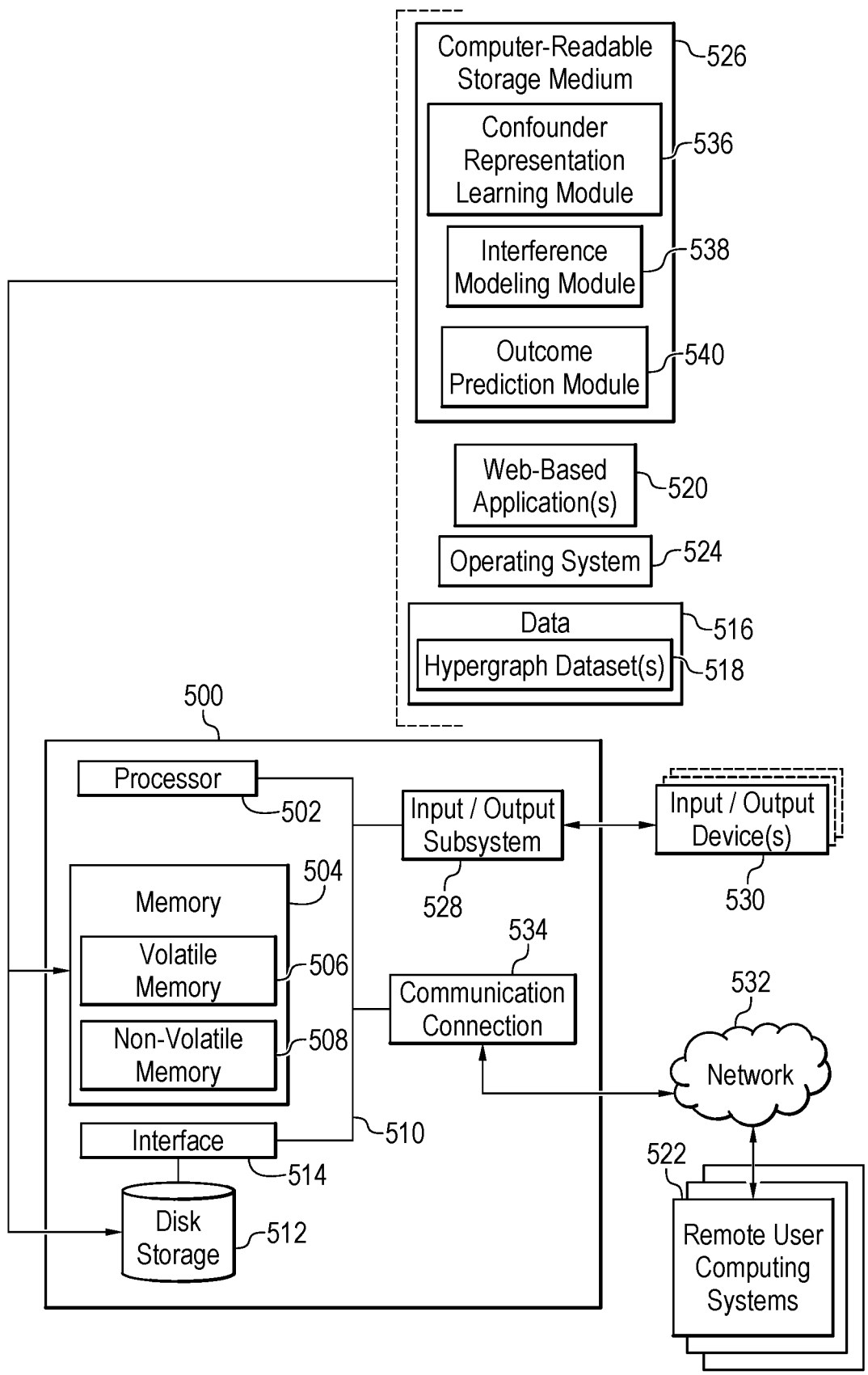
FIG. 5 is a block diagram of an exemplary computing system for implementing the techniques described herein.

Exemplary Computing System and Network Environment for Implementing Techniques Described Herein FIG. 5 is a block diagram of an exemplary computing system 500 for implementing the techniques described herein. The exemplary computing system 500 includes a processor 502 and a memory 504. The processor 502 may include any suitable type of processing unit or device, such as, for example, a single-core processor, a multi-core processor, a computing cluster, or any number of other configurations. Moreover, the processor 502 may include an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combinations thereof, designed to perform the functions described herein.

The memory 504 typically (but not always) includes both volatile memory 506 and non-volatile memory 508. The volatile memory 506 retains or stores information so long as the memory is supplied with power. By contrast, the non-volatile memory 508 is capable of storing (or persisting) information even when a power supply is not available. The volatile memory 506 may include, for example, RAM (e.g., synchronous RAM (SRAM), dynamic RAM (DRAM), synchronous dynamic RAM (SDRAM), and the like) and CPU cache memory. The nonvolatile memory 508 may include, for example, read-only memory (ROM) (e.g., programmable ROM (PROM), electrically programmable ROM (EPROM), electrically erasable ROM (EEROM) or the like), flash memory, nonvolatile random-access memory (RAM), solid-state memory devices, memory storage devices, and/or memory cards.

The processor 502 and the memory 504, as well as other components of the computing system 500, are interconnected by way of a system bus 510. The system bus 510 can be implemented using any suitable bus architecture known to those skilled in the art.

According to the embodiment shown in FIG. 5, the computing system 500 also includes a disk storage 512. The disk storage 512 may include any suitable removable/non-removable, volatile/non-volatile storage component or device. For example, the disk storage 512 may include, but is not limited to, a magnetic disk drive, floppy disk drive, tape drive, Jaz drive, Zip drive, LS-210 drive, flash memory card, memory stick, or the like. In addition, the disk storage 512 may include storage media separately from (or in combination with) other storage media including, but not limited to, an optical disk drive, such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 512 to the system bus 510, a removable or non-removable interface is typically used, such as interface 514 shown in FIG. 5.

In various embodiments, the disk storage 512 and/or the memory 504 function as one or more databases that are used to store data 516 relating to the techniques described herein. Such data 516 include, but are not limited to, one or more hypergraph dataset(s) 518 obtained, for example, from execution of one or more web-based application(s) 520 on any number of remote user computing systems 522, where such remote user computing systems 522 may be operated by users who utilize (or subscribe to) the web-based application(s) 520.

Those skilled in the art will appreciate that FIG. 5 describes software that acts as an intermediary between a user of the computing system 500 and the basic computing resources described with respect to the operating environment of the computing system 500. Such software includes an operating system 524. The operating system 524, which may be stored on the disk storage 512, acts to control and allocate the computing resources of the computing system 500. Moreover, system applications, including the web-based application(s) 520, take advantage of the management of the computing resources by the operating system 524 through one or more program modules stored within a computer-readable storage medium (or media) 526, as described further herein.

The computing system 500 also includes an input/output (I/O) subsystem 528. The I/O subsystem 528 includes a set of hardware, software, and/or firmware components that enable or facilitate inter-communication between the user of the computing system 500 and the processor 502 of the computing system 500. During operation of the computing system 500, the I/O subsystem 528 enables the user to interact with the computing system 500 through various input/output (I/O) devices 530. Such I/O devices 530 may include any number of input devices or channels, such as, for example, one or more touchscreen/haptic input devices, one or more buttons, one or more pointing devices, one or more accessories, one or more audio input devices, and/or one or more video input devices, such as a camera. As an example, in some embodiments, such input devices or channels include one or more Natural User Interface (NUI) devices, where the term "Natural User Interface (NUI)" refers to any interface technology that enables a user to interact with a device in a "natural" manner, free from artificial constraints imposed by input devices such as mice, keyboards, remote controls, and the like. In some examples, NUI devices include devices relying on speech recognition, touch and stylus recognition, gesture recognition both on screen and adjacent to the screen, air gestures, head and eye tracking, voice and speech, vision, touch, gestures, and machine intelligence. For example, NUI devices can include touch-sensitive displays, voice and speech recognition, intention and goal understanding, and motion gesture detection using depth cameras such as stereoscopic camera systems, infrared camera systems, RGB camera systems, and combinations of these. NUI devices can also include motion gesture detection using accelerometers or gyroscopes, facial recognition, three-dimensional (3D) displays, head, eye, and gaze tracking, immersive augmented-reality and virtual-reality systems, all of which provide a more natural interface. Furthermore, in some embodiments the one or more input devices or channels connect to the processor 502 through the system bus 510 via one or more interface ports (not shown) integrated within the I/O subsystem 528. Such interface ports may include, for example, a serial port, a parallel port, a game port, and/or a universal serial bus (USB).

In addition, such I/O devices 530 may include any number of output devices or channels, such as, for example, one or more audio output devices, one or more haptic feedback devices, and/or one or more display devices. Such output devices or channels may use some of the same types of ports as the input devices or channels. Thus, for example, a USB port may be used to both provide input to the computing system 500 and to output information from the computing system 500 to a corresponding output device. Moreover, in some embodiments, the one or more output devices or channels are accessible via one or more adapters (not shown) integrated within the I/O subsystem 528.

In various embodiments, the computing system 500 is communicably coupled to the remote user computing systems 522, which may include, for example, computing systems configured with web browsers, PC applications, mobile phone applications, wearable computing systems (e.g., smart watches and/or other types of wearable computing systems with integrated sensors), and the like, that are utilized by users who utilize (or subscribe to) the web-based application(s) 520. In addition, the remote user computing systems 522 may include, for example, one or more personal computers, one or more servers, one or more routers, one or more network PCs, one or more workstations, one or more microprocessor-based appliances, one or more mobile phones, one or more wearable computing systems, and/or one or more peer devices or other common network nodes. Moreover, in some embodiments, the computing system 500 is a web-based application provider computing system/server hosting the web-based application(s) 520 in a networked environment using logical connections to the remote user computing systems 522, as described further with respect to FIG. 6. In such embodiments, the computing system 500 may provide for execution of the web-based application(s) 520 on the remote user computing systems 522 with the enhanced ITE estimation functionality provided by the techniques described herein.

In various embodiments, the remote user computing systems 522 are logically connected to the computing system 500 through a network 532 and then connected via a communication connection 534, which may be wireless. The network 532 encompasses wireless communication networks, such as local-area networks (LAN) and wide-area networks (WAN). LAN technologies include Fiber Distributed Data Interface (FDDI), Copper Distributed Data Interface (CDDI), Ethernet, Token Ring, and the like. WAN technologies include, but are not limited to, point-to-point links, circuit switching networks like Integrated Services Digital Networks (ISDN) and variations thereon, packet switching networks, and Digital Subscriber Lines (DSL).

The communication connection 534 includes the hardware/software employed to connect the network 532 to the bus 510. While the communication connection 534 is shown for illustrative clarity as residing inside the computing system 500, it can also be external to the computing system 500. The hardware/software for connection to the network 532 may include, for example, internal and external technologies, such as mobile phone switches, modems including regular telephone grade modems, cable modems and DSL modems, ISDN adapters, and/or Ethernet cards.

As described above, system applications, such as the web-based application(s) 520, take advantage of the management of the computing resources by the operating system 524 through one or more program modules stored within the computer-readable storage medium (or media) 526. In some embodiments, the computer-readable storage medium 526 is integral to the computing system 500, in which case it may form part of the memory 504 and/or the disk storage 512. In other embodiments, the computer-readable storage medium 526 is an external device that is connected to the computing system 500 when in use.

In various embodiments, the one or more program modules stored within the computer-readable storage medium 526 include program instructions or code that may be executed by the processor 502 to perform various operations, including the techniques described herein. In various embodiments, such program modules include, but are not limited to, a confounder representation learning module 536, an interference modeling module 538, and an outcome prediction module 540 that cause the processor 502 to perform operations that result in the execution of the techniques described herein for ITE estimation under high-order interference in hypergraphs, as described with respect to the method 400 of FIG. 4, for example.

Figure 6:
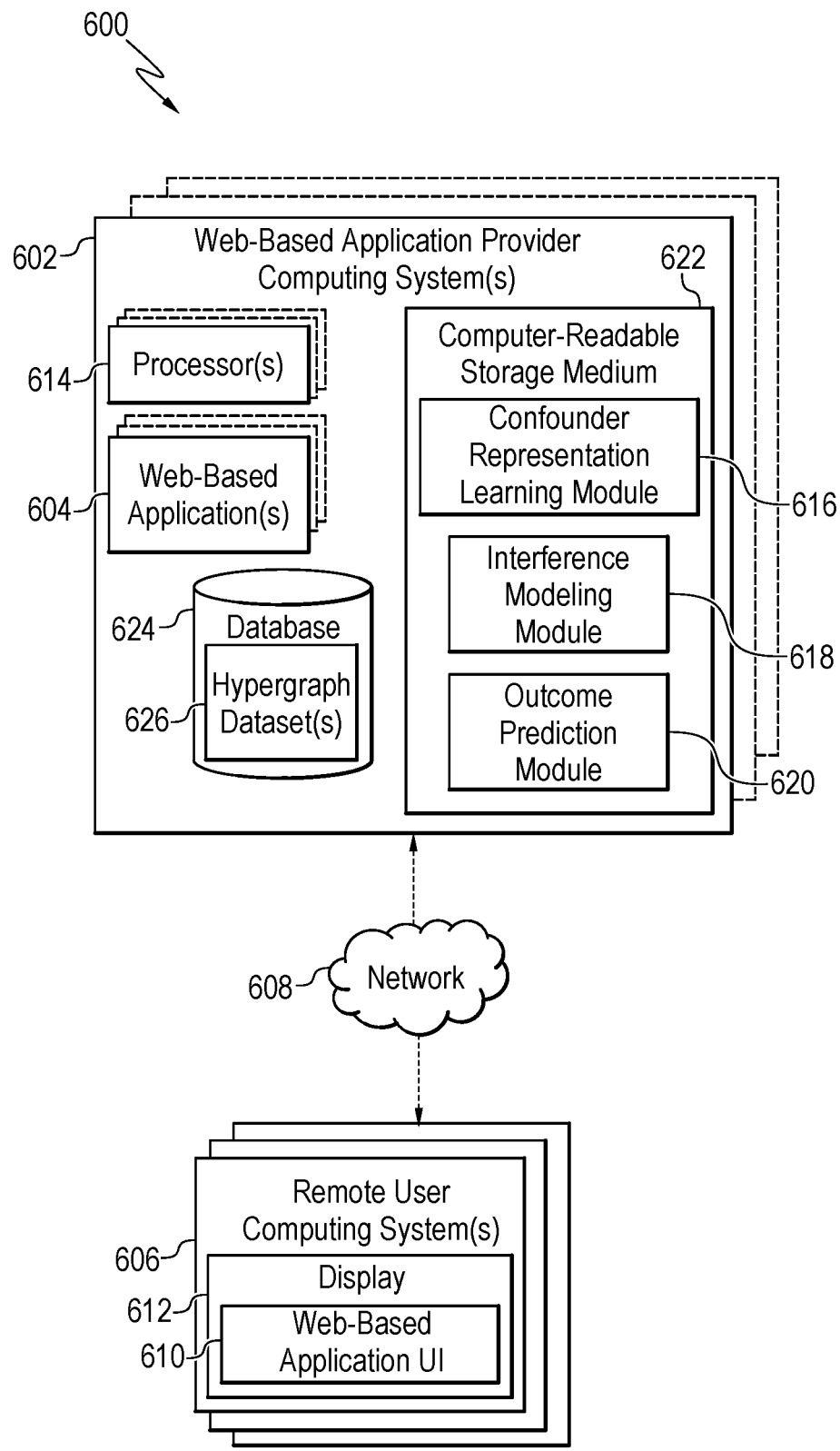
FIG. 6 is a block diagram of an exemplary network environment for implementing the techniques described herein.

As an example, in some embodiments, the execution of the confounder representation learning module 536, the interference modeling module 538, and the outcome prediction module 540 in conjunction with the web-based application(s) 520 may result in the generation of more highly-relevant, user-specific advertisements, recommendations, and the like during execution of the web-based application(s) 520 on the remote user computing systems 522, as described further with respect to FIG. 6. As another example, in some embodiments, the execution of the confounder representation learning module 536, the interference modeling module 538, and the outcome prediction module 540 in conjunction with the web-based application(s) 520 may enable the evaluation of one or more new feature for the web-based application(s) 520 before such features are fully launched. As yet another example, in some embodiments, the execution of the confounder representation learning module 536, the interference modeling module 538, and the outcome prediction module 540 in conjunction with the web-based application(s) 520 may enable the collection of data relating to one or more studies or experiments that involve multi-user interactions.

It is to be understood that the block diagram of FIG. 5 is not intended to indicate that the computing system 500 is to include all of the components shown in FIG. 5. Rather, the computing system 500 can include fewer or additional components not illustrated in FIG. 5 (e.g., additional applications, additional modules, additional memory devices, additional network interfaces, etc.). Furthermore, any of the functionalities of the one or more program modules/submodules may be partially, or entirely, implemented in hardware and/or in the processor 502. For example, the functionality may be implemented with an application specific integrated circuit, in logic implemented in the processor 502, or in any other device.

FIG. 6 is a block diagram of an exemplary network environment 600 for implementing the techniques described herein. As shown in FIG. 6, the network environment 600 includes one or more web-based application provider computing system(s) or server(s) 602 that provide for the execution of one or more web-based application(s) 604 on remote user computing systems 606. In various embodiments, such web-based application(s) may include any applications that involve interactions between three or more users. Non-limiting examples of such applications include social media applications, communication applications, calendar applications, professional networking applications, employee experience applications, and various types of enterprise applications. More specific, non-limiting examples of such applications include Microsoft® Viva®, Microsoft® Teams®, Microsoft® Outlook®, and Microsoft® Yammer®, which are all provided by Microsoft Corporation.

Furthermore, the remote user computing systems 606 may include any suitable types of computing systems operated by users who utilize (or subscribe to) such web-based application(s) 604. Moreover, it is to be understood that the term "web-based application" as used herein is intended to cover other types of interactions between multiple users or items. As an example, the web-based applications may relate to one or more web-based studies regarding particular user/item interactions, such as, for example, studies regarding particular products, media content, health topics, or the like.

In various embodiments, the ITE estimation functionalities described herein are provided to the remote user computing systems 606 via a network 608, which provides a communications link for facilitating the transfer of electronic content between the web-based application provider computing system(s) 602 and the remote user computing systems 606. The network 608 may include, but is not limited to, a cellular network, a point-to-point dial up connection, a satellite network, the Internet, a local area network (LAN), a wide area network (WAN), and/or a Wi-Fi network. Such networks are widely used to connect various types of network elements, such as routers, servers, and gateways. Moreover, those skilled in the art will appreciate that the present techniques may also be practiced in a multi-network environment having various connected public and/or private networks. Furthermore, those skilled in the art will appreciate that communication networks can take several different forms and use several different communication protocols. For example, in some embodiments, the present techniques may be practiced in a distributed computing environment in which tasks are performed by remote processing devices that are linked through a communications network. In a distributed computing environment, program modules can be located in both local and remote computer-readable storage media.

In various embodiments, each remote user computing system 606 includes one or more processors, one or more memory devices, and one or more disk storage devices, as well as an input/output subsystem that operatively couples one or more input/output devices to the processor(s). Moreover, each remote user computing system 606 may include any suitable type of computing device, including, but not limited to, a desktop computer, laptop computer, tablet, mobile phone, wearable computing system (e.g., smart watch), gaming system, television, or the like. Generally speaking, each remote user computing system 606 may include any type of computing device that provides its user with the ability to load and execute software programs, including the web-based application(s) 604, as well as the ability to access the network 608 to communicate with the web-based application provider computing system(s) 602.

In various embodiments, the web-based application provider computing system(s) 602 host one or more web-based application UI(s) 610 on a display 612 of any number of the remote user computing systems 606. In various embodiments, this is accomplished by executing, via one or more processors 614 of the web-based application provider computing system(s) 602, the web-based application(s) 604 in conjunction with a confounder representation learning module 616, an interference modeling module 618, and an outcome prediction module 620 stored within one or more computer-readable storage media 622 of the web-based application provider computing system(s) 602, as described further with respect to FIG. 7. In addition, the web-based application provider computing system(s) 602 may include one or more databases 624 that function as repositories for the data, including one or more hypergraph dataset(s) 626, used by the components of the web-based application provider computing system(s) 602 to perform the ITE estimation techniques described herein.

Those skilled in the art will appreciate that the web-based application UI(s) 610 can be used to collect data relating to any number of different types of multi-user interactions. In addition, the ITE estimation techniques described herein may be utilized to improve the functionality of the corresponding web-based application(s) 604 in any suitable manner.

Furthermore, it is to be understood that the block diagram of FIG. 6 is not intended to indicate that the network environment 600 is to include all of the components shown in FIG. 6. Rather, the network environment 600 can include fewer or additional components not illustrated in FIG. 6. For example, in practice, the web-based application provider computing system(s) 602 and the remote user computing systems 606 will include a number of additional components not depicted in the simplified block diagram of FIG. 6, as described with respect to the computing system 500 of FIG. 5, for example.

Figure 7:
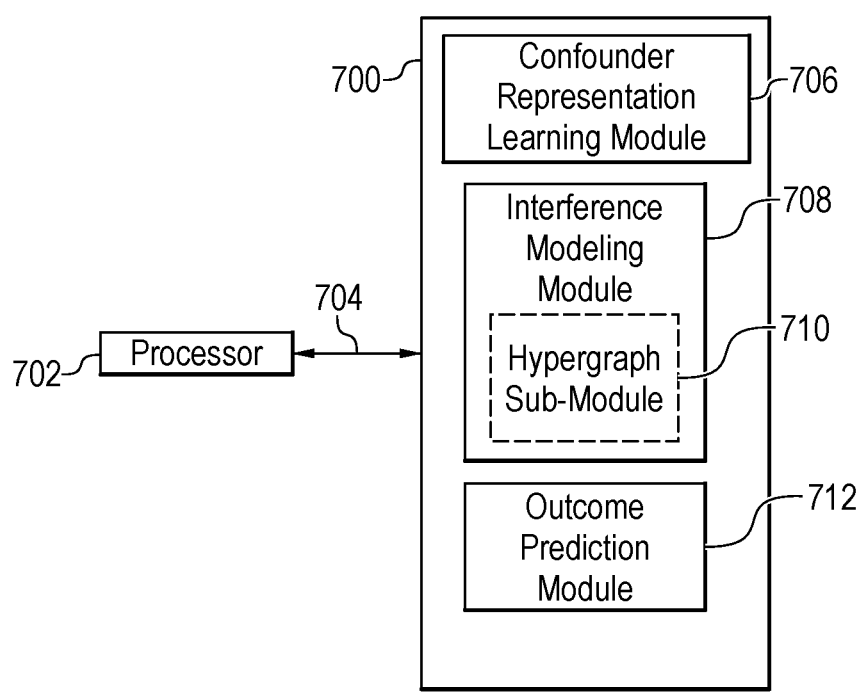
FIG. 7 is a block diagram of an exemplary computer-readable storage medium for implementing the techniques described herein.

FIG. 7 is a block diagram of an exemplary computer-readable storage medium 700 for implementing the techniques described herein. In various embodiments, the computer-readable storage medium 700 is accessed by a processor 702 over a computer interconnect 704. For example, in some embodiments, the computer-readable storage medium 700 is the same as, or similar to, the computer-readable storage medium described with respect to the computing system 500 of FIG. 5 and/or the network environment 600 of FIG. 6.

In various embodiments, the computer-readable storage medium 700 includes code (i.e., computer-executable instructions) to direct the processor 702 to perform the operations of the present techniques. Such code may be stored within the computer-readable storage medium 700 in the form of program modules, where each module includes a set of computer-executable instructions that, when executed by the processor 702, cause the processor 702 to perform a corresponding set of operations. In particular, in various embodiments, the computer-readable storage medium 700 includes a confounder representation learning module 706, an interference modeling module 708 (including a hypergraph sub-module 708), and an outcome prediction module 712, as described herein. Such modules direct the processor 702 to perform the ITE estimation techniques described herein (or any suitable variation thereof), including, but not limited to, the method 400 described with respect to FIG. 4.

Moreover, those skilled in the art will appreciate that the computer-readable storage medium 700 is not limited to the modules/sub-modules shown in FIG. 7. Rather, any number of modules/sub-modules may be added to the computer-readable storage medium 700 or removed from the computer-readable storage medium 700, depending on the details of the specific implementation.

Exemplary Implementations of Techniques Described Herein

The following is a description of exemplary implementations of the techniques described herein for three different semi-synthetic datasets. (Note that the semi-synthetic nature of the datasets is due to the difficulty with obtaining ground-truth counterfactual data, as only one of two potential outcomes can be obtained for observational data). The semi-synthetic datasets are all based on real-world hypergraph data, and the treatment allocations and node features (covariates) are retained (if they are available). The outcome generation process is then simulated to assess the true individual treatment effect (ITE). Moreover, those skilled in the art will appreciate that these exemplary implementations are for illustrative purposes only. In practice, the techniques described herein may be implemented in any other suitable manner to achieve any other suitable results, depending on the details of the particular implementation.

The semi-synthetic datasets include two publicly-available hypergraph datasets (e.g., referred to as the "Contact" dataset and the "Goodreads" dataset) and one large-scale proprietary web-based application dataset (e.g., referred to as the "Microsoft Teams" dataset). The temporal information for each hyperedge is not accounted for in these exemplary implementations, although the techniques described herein can be readily extended to account for such information. In all three datasets, extremely large hyperedges are discarded, and only those with 50 nodes or less are retained.

Turning now to the outcome simulation process, given the treatment allocations T, the node features X, and the hypergraph structure H, the potential outcome of an individual/node i can be simulated according to Equation (16).

$$y_i = f_{y,0}(x_i) + \gamma f_t(t_i, x_i) + \beta f_s(T, X, H) + \epsilon_{y_i} \qquad (16)$$

In Equation (16), $\gamma f_t(t_i, x_i)$ quantifies the individual treatment effect (ITE) for individual i, and $\beta f_s(T, X, H)$ accounts the hypergraph spillover effect. In addition, $f_{y,0}(x_i)$ refers the outcome of instance i when $t_i=0$ and without network interference; $f_t(\cdot)$ calculates the ITE of each instance; $f_s(\cdot)$ calculates the spillover effect; and $\in_{y_i}$ denotes the random noise from a Gaussian distribution $\mathcal{N}(0,1)$. The term $f_{y,0}(x_i)$ is specified as a linear transformation of $x_i$, as shown in Equation (17).

$$f_{y,0}=w_0 x_i \tag{17}$$

In Equation (17), $w_0 \sim \mathcal{N}(0, I)$, $w_0 \in \mathbb{R}^d$. The individual treatment effect ($f_t(t_i, x_i)$) and the hypergraph spillover effect ($f_s(T, X, H)$) are then controlled under two different settings: (1) the linear setting, as defined by Equations (18) and (19), and (2) the quadratic setting, as defined by Equations (20) and (21).

$$f_t(t_i, x_i) = \begin{cases} w_1 x_1 + \epsilon & \text{if } t_i = 1 \\ 0 & \text{if } t_i = 0 \end{cases} \tag{18}$$

Here, $w_1 \in \mathbb{R}^d$, and each element in $w_1$ follows the distribution $\mathcal{N}(0, 0.01)$. Then $f_s$ is generated as shown in Equation (19).

$$f_s(T, X, H) = \frac{1}{|\varepsilon_i|} \sum_{e \in \varepsilon_i} \sigma\left(\frac{1}{|\mathcal{N}_e|} \sum_{j \in \mathcal{N}_e} t_j \times f_t(t_j, x_j)\right) \tag{19}$$

Turning now to the quadratic setting, in Equation (20), $W_t \in \mathbb{R}^{d \times d}$, and each element in $W_t$ follows the distribution $\mathcal{N}(0, 0.01)$.

$$f_t(t_i, x_i) = \begin{cases} x_i^T W_t x_i + \epsilon & \text{if } t_i = 1 \\ 0 & \text{if } t_i = 0 \end{cases} \tag{20}$$

Then $f_s$ is generated as shown in Equation (21).

$$f_s(T, X, H) = \frac{1}{|\varepsilon_i|} \sum_{e \in \varepsilon_i} \frac{1}{|\mathcal{N}_e|^2} \left((T_e * X_e) w_t (T_e * X_e)^T\right) \tag{21}$$

Here, $X_e$ and $T_e$ are the feature matrix and treatment assignment of nodes contained in hyperedge e, respectively. In addition, * denotes element-wise multiplication. According to exemplary implementation described herein, the above process is followed to generate potential outcomes on all three datasets.

The following discussion provides details about each dataset that was utilized according to the exemplary implementation described herein. First, the Contact dataset was formed by collecting information about interactions recorded by wearable sensors (e.g., wearable sensors integrated within smart watches or other types of wearable computing systems) among students at a high school. The Contact dataset includes 327 nodes and 7,818 hyperedges. The average node degree in this dataset is 55.6, and the average hypergraph size is 2.3. Each node represents a person, and each hyperedge stands for a group of individuals that are in close physical proximity to each other. The goal was to determine the manner in which one's face covering practice (e.g., treatment) causally affect one's infection risk of (e.g., outcome). In each group contact, one may bring the virus to the surrounding environment, and thus affect other people's infection risk. Due to the lack of detailed information about each individual, apart from the potential outcome, the treatment ($t_i$) and the covariates ($x_i$) are generated as shown in Equation (22).

$$x_i \sim \mathcal{N}(0,I), t_i \sim Ber(\text{sigmoid}(x_i v_t)) \tag{22}$$

In Equation (22), I is a d×d identity matrix, with d=50 for this example. In addition, $v_t$ is a d-dimensional vector, where each element inside follows the Gaussian distribution $\mathcal{N}(0, 0.5)$. Eventually, 50% of the nodes are treated ($t_i=1$) in the experimental implementation.

The GoodReads dataset was formed by collecting book information from the book review website "GoodReads", including the book title, authors, descriptions, reviews, and ratings. Each book in the "Children" category is used as an instance. The bag-of-words of the book descriptions are used as the covariates of each book. Each hyperedge corresponds to each author, and all books sharing the same author are in the same hyperedge. The real-world book ratings are considered as treatment assignments, with t=1 if the rating score is larger than 3 and t=0 otherwise. The goal was to study the causal effect of the rating score on the sales of each book. The ratings of each author's books can establish the author's overall reputation, thus influencing the sales of other books from the same author. The final processed dataset includes 57,031 nodes (where 40% are treated), as well as 12,709 hyperedges. Note that each book may have more than one author (the average node degree is 1.36), and each author may have published multiple books (the average hyperedge size is 5.76).

For the Microsoft Teams dataset, 91,391 anonymized Microsoft employees were sampled, and their aggregated telemetry data corresponding to the workplace communication platform/web-based application Microsoft Teams was aggregated. On this platform, users are allowed to create a group space (i.e., "team" or "channel") to enable public communication within each group. The goal was to determine the manner in which a user's usage of these group spaces causally affects their productivity. The treatment assignment was processed into binary values by assigning the treatment as 1 if the employee sent out at least one message in any of these group spaces during the first week of March 2021; otherwise, the treatment was assigned as 0. Each group space can be regarded as a hyperedge, where information can be shared via group discussions and, thus, one's activeness on this platform may affect other individuals' outcomes in the same group. Employee demographics (e.g., office location, job description, work experience, and the like) are leveraged as the covariates.

For the experimental implementation described herein, the performance of causal effect estimation is evaluated through two standard metrics, including Rooted Precision in Estimation of Heterogeneous Effect ($\sqrt{\epsilon_{PEHE}}$) and Mean Absolute Error ($\epsilon_{ATE}$). These metrics can be defined as shown in Equation (23).

$$\sqrt{\epsilon_{PEHE}} = \sqrt{\frac{1}{n}\sum_{i \in [n]}(\tau_i - \hat{\tau}_i)^2}, \epsilon_{ATE} = \left|\frac{1}{n}\sum_{i \in [n]}\tau_i - \frac{1}{n}\sum_{i \in [n]}\hat{\tau}_i\right| \tag{23}$$

For these metrics, a lower $\sqrt{\epsilon_{PEHE}}$ or a lower $\epsilon_{ATE}$ indicates a better causal effect estimation.

To investigate the effectiveness of the present techniques, the results of the present techniques are compared to the results of multiple previous ITE estimation techniques. Such previous ITE estimation techniques can be divided into three categories: (1) no-graph ITE estimation techniques; (2)

no-spillover-effect-in-ordinary-graphs ITE estimation techniques; and (3) spillover-effect-in-ordinary-graphs ITE estimation techniques. First, with regard to the no-graph ITE estimation techniques, the estimation results are compared with results from previous methods that do not consider graph data or spillover effects. Such previous methods include outcome regression, which is implemented by linear regression (LR), counterfactual regression (CFR), and causal effect variational autoencoder (CEVAE). Second, with regard to the no-spillover-effect-in-ordinary-graphs ITE estimation techniques, assuming no spillover effect exists, the network deconfounder (Netdeconf) captures latent confounders for ITE estimation by utilizing the network structure among instances. Third, with regard to the utilized. By default, one hypergraph convolutional layer is used for the interference modeling component.

The results for the ITE estimation task are provided in Table 2, which shows a comparison of the ITE estimation performance (in terms of mean±standard error) for the three datasets. From Table 2, it is observed that the proposed framework (HyperSCI) outperforms all the baselines under both linear and quadratic outcome simulation settings. These results are attributable, at least in part, to the fact that the present techniques utilize the relational information in hypergraphs to model the high-order interference, and thus mitigate the potential biases in ITE estimation that are caused by the spillover effect.

TABLE 2

| Data | Method | Linear | | Quadratic | |
|---|---|---|---|---|---|
| | | $\sqrt{\epsilon_{PEHE}}$ | $\epsilon_{ATE}$ | $\sqrt{\epsilon_{PEHE}}$ | $\epsilon_{ATE}$ |
| Contact | LR | 25.41 ± 0.04 | 9.11 ± 0.09 | 38.22 ± 0.77 | 20.28 ± 0.38 |
| | CEVAE | 22.88 ± 1.07 | 8.29 ± 0.69 | 35.28 ± 0.75 | 18.22 ± 0.76 |
| | CFR | 24.04 ± 0.75 | 7.17 ± 0.43 | 32.24 ± 1.01 | 17.28 ± 0.75 |
| | Netdeconf | 10.22 ± 0.47 | 4.29 ± 0.13 | 21.23 ± 0.72 | 11.39 ± 0.74 |
| | GNN-HSIC | 7.42 ± 0.39 | 2.06 ± 0.03 | 16.28 ± 0.24 | 7.28 ± 0.39 |
| | GCN-HSIC | 7.28 ± 0.44 | 2.08 ± 0.04 | 14.23 ± 0.20 | 6.27 ± 0.15 |
| | HyperSCI | 3.45 ± 0.27 | 1.39 ± 0.03 | 9.20 ± 0.09 | 2.24 ± 0.07 |
| GoodReads | LR | 23.01 ± 0.04 | 13.42 ± 0.12 | 48.56 ± 1.02 | 31.19 ± 0.47 |
| | CEVAE | 22.69 ± 0.03 | 12.49 ± 0.06 | 45.21 ± 3.10 | 29.22 ± 0.44 |
| | CFR | 20.30 ± 0.03 | 13.21 ± 0.09 | 41.72 ± 0.72 | 26.28 ± 0.43 |
| | Netdeconf | 18.39 ± 0.19 | 12.20 ± 0.03 | 35.18 ± 0.78 | 21.20 ± 0.76 |
| | GNN-HSIC | 17.20 ± 0.23 | 12.18 ± 0.13 | 27.22 ± 0.78 | 16.87 ± 0.47 |
| | GCN-HSIC | 16.01 ± 0.20 | 12.06 ± 0.15 | 25.42 ± 0.76 | 16.28 ± 0.76 |
| | HyperSCI | 15.68 ± 0.21 | 11.81 ± 0.15 | 19.23 ± 0.44 | 13.33 ± 0.27 |
| Microsoft Teams | LR | 22.80 ± 0.64 | 21.41 ± 0.74 | 414.17 ± 3.94 | 192.80 ± 2.97 |
| | CEVAE | 19.36 ± 0.80 | 8.63 ± 0.78 | 315.01 ± 2.53 | 188.47 ± 4.27 |
| | CFR | 25.23 ± 0.01 | 18.28 ± 0.02 | 392.56 ± 4.33 | 189.75 ± 4.80 |
| | Netdeconf | 11.11 ± 0.01 | 9.22 ± 0.03 | 241.02 ± 2.32 | 147.29 ± 1.04 |
| | GNN-HSIC | 9.38 ± 0.44 | 6.91 ± 0.38 | 114.28 ± 3.62 | 81.21 ± 2.53 |
| | GCN-HSIC | 8.27 ± 0.41 | 6.60 ± 0.48 | 109.57 ± 3.85 | 77.75 ± 3.93 |
| | HyperSCI | 5.13 ± 0.56 | 4.46 ± 0.61 | 81.08 ± 0.37 | 74.41 ± 0.42 | spillover-effect-in-ordinary-graphs ITE estimation techniques, the results of the present techniques are compared to the results of other ITE estimation techniques that can handle the pairwise spillover effect on ordinary graphs. For example, a node-representation-learning-based method estimates ITE under network interference, including two variants: (1) GNN+HSIC, which is based on graph neural networks and the Hilbert Schmidt independence criterion (HSIC); and (2) GCN+HSIC, which is based on graph convolutional networks and the HSIC. Moreover, to utilize the previous techniques that handle ordinary graphs, the original hypergraph $\mathcal{H}$ is projected to an ordinary graph $\mathcal{G} = \{\mathcal{V}, \varepsilon^P\}$ by setting $(v_i, v_j) \in \varepsilon^P$ if $v_i$ and $v_j$ are contained in at least one common hyperedge in $\mathcal{H}$. By comparing the present techniques to such previous techniques, it is possible to evaluate the effectiveness of modeling high-order interferences on hypergraphs according to the present techniques.

Figure 8B:
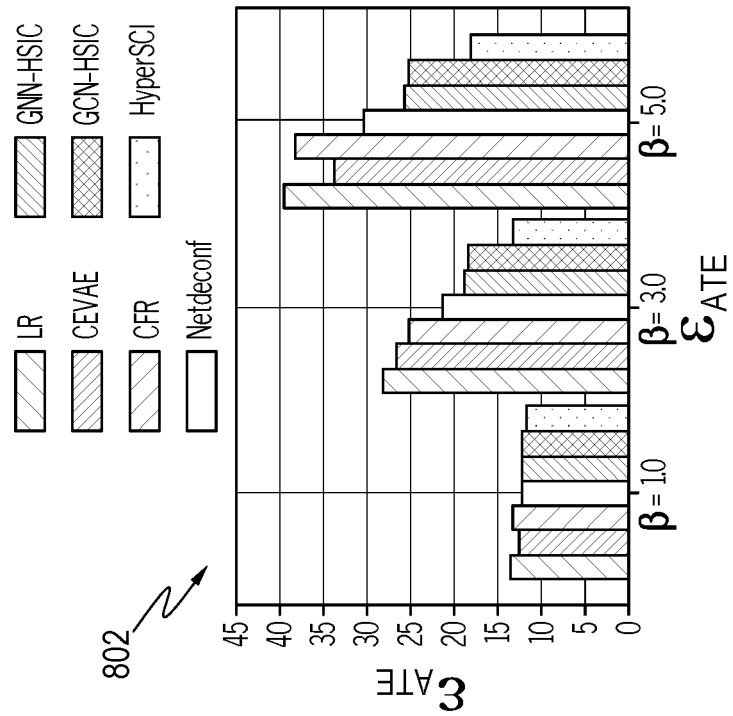
FIG. 8B is a graph showing a comparison of the ITE estimation performance under different values of the hyper-parameter ($\beta$) in the linear setting for the GoodReads dataset, where Mean Absolute Error ($\epsilon_{ATE}$) is used as the metric for evaluation.
Figure 8A:
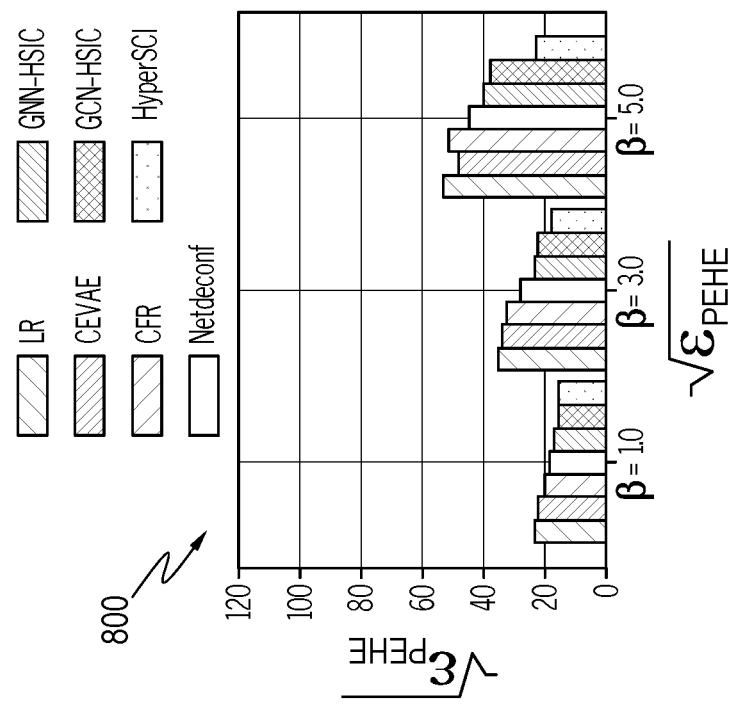
FIG. 8A is a graph showing a comparison of the ITE estimation performance under different values of the hyper-parameter ($\beta$) in the linear setting for the GoodReads dataset, where Rooted Precision in Estimation of Heterogeneous Effect ($\sqrt{\epsilon_{PEHE}}$) is used as the metric for evaluation.

To set up the experimental implementations, all three datasets are randomly partitioned into 60%/20%/20% training/validation/test splits. All the results are averaged over ten repeated executions. Unless otherwise specified, the hyperparameters are set as α=0.001, β=1.0, γ=1.0, λ=0.01, and the dimension for confounder representation and interference representation are both set as 64. LeakyReLU function is used to implement σ(•), and an Adam optimizer is As part of the experimental implementation, the hyperparameter (β), which controls the significance of the hypergraph spillover effect in the outcome simulation, was varied. The corresponding ITE estimation results are reported in FIGS. 8A and 8B. Specifically, FIG. 8A is a graph 800 showing a comparison of the ITE estimation performance under different values of the hyperparameter (β) in the linear setting for the GoodReads dataset, where $\sqrt{\epsilon_{PEHE}}$ is used as the metric for evaluation. Similarly, FIG. 8B is a graph 802 showing a comparison of the ITE estimation performance under different values of the hyperparameter (β) in the linear setting for the GoodReads dataset, where $\epsilon_{ATE}$ is used as the metric for evaluation. As shown in FIGS. 8A and 8B, as β increases (i.e., as the outcome is more heavily influenced by interference), larger performance gains can be observed from the framework described herein (HyperSCI) as compared to previous frameworks. This observation further validates the effectiveness of the present techniques in modeling the high-order interference for enhancing the performance of ITE estimation.

It should be noted that, while the methods and processes described herein are generally expressed in regard to discrete steps, these steps should be viewed as being logical in nature and may or may not correspond to any specific actual and/or discrete steps of a given implementation. In addition, the order in which these steps are presented in the various methods and processes, unless otherwise indicated, should not be construed as the only order in which the steps may be carried out. Moreover, in some instances, some of these steps may be combined and/or omitted. Those skilled in the art will recognize that the logical presentation of steps is sufficiently instructive to carry out aspects of the claimed subject matter irrespective of any particular development or coding language in which the logical instructions/steps are encoded.

Of course, while the methods and processes described herein include various novel features of the disclosed subject matter, other steps (not listed) may also be carried out in the execution of the subject matter set forth in these methods and processes. Those skilled in the art will appreciate that the logical steps of these methods and processes may be combined together or split into additional steps. Steps of the above-described methods and processes may be carried out in parallel or in series. Often, but not exclusively, the functionality of a particular method or process is embodied in software (e.g., applications, system services, libraries, and the like) that is executed on one or more processors of computing systems. Additionally, in various embodiments, all or some of the various methods and processes may also be embodied in executable hardware modules including, but not limited to, system on chips (SoC's), codecs, specially designed processors and/or logic circuits, and the like, on a computing system.

As suggested above, each method or process described herein is typically embodied within computer-executable instruction (or code) modules including individual routines, functions, looping structures, selectors, and switches (such as if-then and if-then-else statements), assignments, arithmetic computations, and the like, that, in execution, configure a computing system to operate in accordance with the particular method or process. However, as suggested above, the exact implementation in executable statement of each of the methods or processes is based on various implementation configurations and decisions, including programming languages, compilers, target processors, operating environments, and the linking or binding operation. Those skilled in the art will readily appreciate that the logical steps identified in these methods and processes may be implemented in any number of ways and, thus, the logical descriptions set forth above are sufficiently enabling to achieve similar results.

While various novel aspects of the disclosed subject matter have been described, it should be appreciated that these aspects are exemplary and should not be construed as limiting. Variations and alterations to the various aspects may be made without departing from the scope of the disclosed subject matter.

EXAMPLES

Example 1 is a method for ITE estimation under high-order interference in hypergraphs. The method is implemented in a computing system including a processor. The method includes: accessing, via the processor, a hypergraph dataset including multi-way interactions among nodes within each hyperedge of a corresponding hypergraph, where the hypergraph dataset corresponds to a treatment assignment for each node; performing representation learning on the hypergraph dataset to control for confounders corresponding to features of each node and to learn a confounder representation for each node; modeling a high-order interference representation for each node by propagating the learned confounder representation and the treatment assignment for each node with a hypergraph convolutional layer, while utilizing a hypergraph attention mechanism to assign an attention score to each node, where the attention score corresponds to a significance of interference for the corresponding node; and estimating an ITE for each node under the treatment assignment based on the learned confounder representation and the modeled high-order interference representation for each node.

Example 2 includes the method of example 1, including or excluding optional features. In this example, the method includes executing, via a network, a web-based application on remote computing systems and collecting, via the network, hypergraph data for the hypergraph dataset during the execution of the web-based application.

Example 3 includes the method of example 2, including or excluding optional features. In this example, the web-based application includes a social media application, a communication application, a calendar application, a professional networking application, an employee experience application, a health application, a fitness application, or some combination thereof.

Example 4 includes the method of example 2, including or excluding optional features. In this example, the nodes of the hypergraph corresponds to users of the remote computing systems, and the multi-way interactions among the nodes within each hyperedge comprise multi-way interactions between the users of the remote computing systems during the execution of the web-based application.

Example 5 includes the method of example 4, including or excluding optional features. In this example, the remote computing systems include wearable computing systems, and the multi-way interactions between the users include interactions recorded by sensors integrated within the wearable computing systems.

Example 6 includes the method of example 4, including or excluding optional features. In this example, the method further includes utilizing the estimated ITE for each node to enhance a functionality of the web-based application.

Example 7 includes the method of example 6, including or excluding optional features. In this example, enhancing the functionality of the web-based application includes utilizing the estimated ITE for each node to calculate a user-specific parameter for the web-based application and personalizing one or more features of the web-based application with respect to the corresponding user based on the calculated user-specific parameter.

Example 8 includes the method of example 7, including or excluding optional features. In this example, personalizing the feature(s) of the web-based application based on the calculated user-specific parameter includes automatically tailoring advertisements and/or recommendations to the corresponding user.

Example 9 includes the method of example 6, including or excluding optional features. In this example, enhancing the functionality of the web-based application includes utilizing the estimated ITE for each node to calculate a parameter corresponding to the multi-way interactions between the users and modifying the functionality of the web-based application to optimize the parameter.

Example 10 includes the method of any one of examples 1 to 9, including or excluding optional features. In this example, performing the representation learning on the hypergraph dataset includes encoding the features of the nodes into a latent space using an MLP technique, resulting in a set of confounder representations for the nodes that capture potential confounders.

Example 11 includes the method of any one of examples 1 to 10, including or excluding optional features. In this example, performing the representation learning on the hypergraph dataset further includes performing representation balancing on the learned confounder representations to mitigate discrepancies between distributions of the learned confounder representations. In addition, in this example, modeling the high-order interference representation for each node further includes performing representation balancing on the modeled high-order interference representations to mitigate discrepancies between distributions of the modeled high-order interference representations.

Example 12 is a computing system. The computing system includes a processor, a web-based application, and a communication connection for connecting remote computing systems to the computing system through a network, where each remote computing system corresponds to a user who engages in multi-way interactions using the web-based application. The computing system also includes a database for storing a hypergraph dataset including hypergraph data corresponding to the multi-way interactions between the users of the remote computing systems, where each user is represented as a node within the corresponding hypergraph. The computing system further includes a computer-readable storage medium operatively coupled to the processor. The computer-readable storage medium includes computer-executable instructions that, when executed by the processor, cause the processor to: perform representation learning on the hypergraph dataset to control for confounders corresponding to features of each node and to learn a confounder representation for each node; model a high-order interference representation for each node by propagating the learned confounder representation and the treatment assignment for each node with a hypergraph convolutional layer, while utilizing a hypergraph attention mechanism to assign an attention score to each node, where the attention score corresponds to a significance of interference for the corresponding node; estimate an ITE for each node under the treatment assignment based on the learned confounder representation and the modeled high-order interference representation for each node; and utilize the estimated ITE for each node to enhance a functionality of the web-based application with respect to the corresponding user.

Example 13 includes the computing system of example 12, including or excluding optional features. In this example, the web-based application includes a social media application, a communication application, a calendar application, a professional networking application, an employee experience application, a health application, a fitness application, or some combination thereof.

Example 14 includes the computing system of example 12 or 13, including or excluding optional features. In this example, the computer-executable instructions, when executed by the processor, cause the processor to utilize the estimated ITE for each node to enhance the functionality of the web-based application with respect to the corresponding user by utilizing the estimated ITE to calculate a user-specific parameter for the web-based application and personalizing one or more features of the web-based application based on the calculated user-specific parameter.

Example 15 includes the computing system of example 12 or 13, including or excluding optional features. In this example, the computer-executable instructions, when executed by the processor, cause the processor to utilize the estimated ITE for each node to enhance the functionality of the web-based application by utilizing the estimated ITE for each node to calculate a parameter corresponding to the multi-way interactions between the users and modifying functionality of the web-based application to optimize the parameter.

Example 16 includes the computing system of any one of examples 12 to 15, including or excluding optional features. In this example, the computer-executable instructions, when executed by the processor, cause the processor to perform the representation learning on the hypergraph dataset by: encoding the features of the nodes into a latent space using an MLP technique, resulting in a set of confounder representations for the nodes that capture potential confounders; and performing representation balancing on the learned confounder representations to mitigate discrepancies between distributions of the learned confounder representations.

Example 17 is computer-readable storage medium including computer-executable instructions that, when executed by a processor, cause the processor to: access a hypergraph dataset including multi-way interactions among nodes within each hyperedge of a corresponding hypergraph, where the hypergraph dataset corresponds to a treatment assignment for each node; perform representation learning on the hypergraph dataset to control for confounders corresponding to features of each node and to learn a confounder representation for each node; model a high-order interference representation for each node by propagating the learned confounder representation and the treatment assignment for each node with a hypergraph convolutional layer, while utilizing a hypergraph attention mechanism to assign an attention score to each node, where the attention score corresponds to a significance of interference for the corresponding node; and estimate an ITE for each node under the treatment assignment based on the learned confounder representation and the modeled high-order interference representation for each node.

Example 18 includes the computer-readable storage medium of example 17, including or excluding optional features. In this example, the computer-executable instructions, when executed by a processor, cause the processor to collect hypergraph data for the hypergraph dataset via execution of a web-based application on remote computing systems, where the multi-way interactions among the nodes within each hyperedge include interactions between users of the remote computing systems.

Example 19 includes the computer-readable storage medium of example 18, including or excluding optional features. In this example, the computer-executable instructions, when executed by a processor, cause the processor to utilize the estimated ITE for each node to enhance a functionality of the web-based application.

Example 20 includes the computer-readable storage medium of example 19, including or excluding optional features. In this example, the computer-executable instructions, when executed by a processor, cause the processor to enhance the functionality of the web-based application by utilizing the estimated ITE for each node to calculate a user-specific parameter for the web-based application and personalizing one or more features of the web-based application with respect to the corresponding user based on the calculated user-specific parameter.

In particular and in regard to the various functions performed by the above described components, devices, circuits, systems and the like, the terms (including a reference to a "means") used to describe such components are intended to correspond, unless otherwise indicated, to any component which performs the specified function of the described component, e.g., a functional equivalent, even though not structurally equivalent to the disclosed structure, which performs the function in the herein illustrated exemplary aspects of the claimed subject matter. In this regard, it will also be recognized that the innovation includes a system as well as a computer-readable storage media having computer-executable instructions for performing the acts and events of the various methods of the claimed subject matter.

There are multiple ways of implementing the claimed subject matter, e.g., an appropriate API, tool kit, driver code, operating system, control, standalone or downloadable software object, etc., which enables applications and services to use the techniques described herein. The claimed subject matter contemplates the use from the standpoint of an API (or other software object), as well as from a software or hardware object that operates according to the techniques set forth herein. Thus, various implementations of the claimed subject matter described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and additional components, and according to various permutations and combinations of the foregoing. Sub-components can also be implemented as components communicatively coupled to other components rather than included within parent components (hierarchical).

Additionally, it can be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the claimed subject matter may have been disclosed with respect to one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method for individual treatment effect (ITE) estimation under high-order interference in hypergraphs, wherein the method is implemented in a computing system comprising a processor, and wherein the method comprises:
accessing, via the processor, a hypergraph dataset comprising multi-way interactions among nodes within each hyperedge of a corresponding hypergraph, wherein the hypergraph dataset corresponds to a treatment assignment for each node;
performing representation learning on the hypergraph dataset to:
control for confounders corresponding to features of each node; and
learn a confounder representation for each node;
modeling a high-order interference representation for each node by propagating the learned confounder representation and the treatment assignment for each node with a hypergraph convolutional layer of a hypergraph neural network, while utilizing a hypergraph attention mechanism to assign an attention score to each node, wherein the attention score corresponds to a significance of interference for the corresponding node;
estimating an ITE for each node under the treatment assignment based on the learned confounder representation and the modeled high-order interference representation for each node; and
utilizing the estimated ITE for each node to enhance a functionality of a web-based application;
wherein performing the representation learning on the hypergraph dataset further comprises performing representation balancing on the learned confounder representations to mitigate discrepancies between distributions of the learned confounder representations; and
wherein modeling the high-order interference representation for each node further comprises performing representation balancing on the modeled high-order interference representations to mitigate discrepancies between distributions of the modeled high-order interference representations.

2. The method of claim 1, comprising:
executing, via a network, the web-based application on remote computing systems; and
collecting, via the network, hypergraph data for the hypergraph dataset during the execution of the web-based application.

3. The method of claim 2, wherein the web-based application comprises at least one of a social media application, a communication application, a calendar application, a professional networking application, an employee experience application, a health application, or a fitness application.

4. The method of claim 2, wherein the nodes of the hypergraph corresponds to users of the remote computing systems, and wherein the multi-way interactions among the nodes within each hyperedge comprise multi-way interactions between the users of the remote computing systems during the execution of the web-based application.

5. The method of claim 4, wherein the remote computing systems comprise wearable computing systems, and wherein the multi-way interactions between the users comprise interactions recorded by sensors integrated within the wearable computing systems.

6. The method of claim 4, wherein enhancing the functionality of the web-based application comprises:
utilizing the estimated ITE for each node to calculate a user-specific parameter for the web-based application; and
personalizing at least one feature of the web-based application with respect to the corresponding user based on the calculated user-specific parameter.

7. The method of claim 6, wherein personalizing the at least one feature of the web-based application based on the calculated user-specific parameter comprises automatically tailoring at least one of advertisements or recommendations to the corresponding user.

8. The method claim 4, wherein enhancing the functionality of the web-based application comprises:
utilizing the estimated ITE for each node to calculate a parameter corresponding to the multi-way interactions between the users; and
modifying the functionality of the web-based application to optimize the parameter.

9. The method of claim 1, wherein performing the representation learning on the hypergraph dataset comprises encoding the features of the nodes into a latent space using a multilayer perceptron (MLP) technique, resulting in a set of confounder representations for the nodes that capture potential confounders.

10. A computer-readable storage medium comprising computer-executable instructions that, when executed by a processor, cause the processor to:
   access a hypergraph dataset comprising multi-way interactions among nodes within each hyperedge of a corresponding hypergraph, wherein the hypergraph dataset corresponds to a treatment assignment for each node;
   perform representation learning on the hypergraph dataset to:
      control for confounders corresponding to features of each node; and
      learn a confounder representation for each node;
   model a high-order interference representation for each node by propagating the learned confounder representation and the treatment assignment for each node with a hypergraph convolutional layer of a hypergraph neural network, while utilizing a hypergraph attention mechanism to assign an attention score to each node, wherein the attention score corresponds to a significance of interference for the corresponding node;
   estimate an individual treatment effect (ITE) for each node under the treatment assignment based on the learned confounder representation and the modeled high-order interference representation for each node; and
   utilize the estimated ITE for each node to enhance a functionality of a web-based application;
   wherein the computer-executable instructions, when executed by the processor, further cause the processor to:
      perform the representation learning on the hypergraph dataset by performing representation balancing on the learned confounder representations to mitigate discrepancies between distributions of the learned confounder representations; and
      model the high-order interference representation for each node by performing representation balancing on the modeled high-order interference representations to mitigate discrepancies between distributions of the modeled high-order interference representations.

11. The computer-readable storage medium of claim 10, wherein the computer-executable instructions, when executed by the processor, cause the processor to collect hypergraph data for the hypergraph dataset via execution of the web-based application on remote computing systems, and wherein the multi-way interactions among the nodes within each hyperedge comprise interactions between users of the remote computing systems.

12. The computer-readable storage medium of claim 11, wherein the computer-executable instructions, when executed by the processor, cause the processor to enhance the functionality of the web-based application by:
   utilizing the estimated ITE for each node to calculate a user-specific parameter for the web-based application; and
   personalizing at least one feature of the web-based application with respect to the corresponding user based on the calculated user-specific parameter.

\* \* \* \* \*